(12) United States Patent
Pretre et al.

(10) Patent No.: US 10,816,525 B2
(45) Date of Patent: *Oct. 27, 2020

(54) METHOD AND MEASURING APPARATUS FOR DETERMINING PHYSICAL PROPERTIES OF GAS

(71) Applicant: MEMS AG, Brugg (CH)

(72) Inventors: Philippe Pretre, Dattwil (CH); Andreas Kempe, Zurich (CH); Tobias Suter, Kilchberg (CH)

(73) Assignee: MEMS AG, Brugg (CH)

( * ) Notice: Subject to any disclaimer, the term of this patent is extended or adjusted under 35 U.S.C. 154(b) by 153 days.

This patent is subject to a terminal disclaimer.

(21) Appl. No.: 15/610,000

(22) Filed: May 31, 2017

(65) Prior Publication Data
US 2017/0261480 A1 Sep. 14, 2017

Related U.S. Application Data

(63) Continuation-in-part of application No. 15/446,783, filed on Mar. 1, 2017, now abandoned, which is a
(Continued)

(30) Foreign Application Priority Data

May 24, 2013 (EP) ..................... 13002708

(51) Int. Cl.
*G01N 25/00* (2006.01)
*G01N 33/00* (2006.01)
(Continued)

(52) U.S. Cl.
CPC ........... *G01N 33/0062* (2013.01); *G01N 7/00* (2013.01); *G01N 25/18* (2013.01); *G01N 25/36* (2013.01);
(Continued)

(58) Field of Classification Search
CPC ...... G01N 25/18; G01N 25/36; G01N 25/005; G01N 33/0062; G01N 33/225; G01N 7/00; G01F 15/04; G01F 15/043; G01F 15/046

See application file for complete search history.

(56) References Cited

U.S. PATENT DOCUMENTS

| 4,154,099 A | 5/1979 | Blu et al. |
| 4,384,792 A | 5/1983 | Sommers et al. |

(Continued)

FOREIGN PATENT DOCUMENTS

| EP | 0 591 639 | 4/1994 |
| EP | 1 265 068 | 12/2002 |

(Continued)

OTHER PUBLICATIONS

Web page titled "Sonic Nozzles" available at https://www.flowsystemsinc.com/sonic-nozzles-and-critical-flow-venturis/ and retrieved on Oct. 2, 2019.*

(Continued)

*Primary Examiner* — Blake A Tankersley
(74) *Attorney, Agent, or Firm* — Nixon & Vanderhye P.C.

(57) ABSTRACT

A method using a gas reservoir and a critical nozzle for determining physical properties and/or quantities relevant to combustion of gas or gas mixtures, the method includes: flowing a gas or gas mixture under pressure from the gas reservoir through the critical nozzle; measuring pressure drop in the gas reservoir as a function of time; determining a gas property factor ($\Gamma^*$), dependent on physical properties of the gas or gas mixture, based on the measured values of the pressure drop; and determining a desired physical property or quantity relevant to combustion based on the gas property factor ($\Gamma^*$) through correlation.

24 Claims, 8 Drawing Sheets

Related U.S. Application Data continuation of application No. 14/282,562, filed on May 20, 2014, now Pat. No. 9,612,229.

(51) Int. Cl.
*G01N 25/36* (2006.01)
*G01N 7/00* (2006.01)
*G01N 33/22* (2006.01)
*G01N 25/18* (2006.01)

(52) U.S. Cl.
CPC ......... *G01N 33/225* (2013.01); *G01N 25/005* (2013.01); *Y10T 29/49321* (2015.01)

(56) References Cited

U.S. PATENT DOCUMENTS

| | | | |
|---|---|---|---|
| 5,307,668 A * | 5/1994 | Vander Heyden | G01N 7/00 73/23.28 |
| 5,311,447 A | 5/1994 | Bonne | |
| 6,442,996 B1 | 9/2002 | Thurston et al. | |
| 7,104,112 B2 | 9/2006 | Bonne | |
| 7,377,152 B2 | 5/2008 | Brekelmans et al. | |
| 7,536,908 B2 | 5/2009 | Wang | |
| 7,730,766 B2 | 6/2010 | Ryser et al. | |
| 7,871,826 B2 | 1/2011 | Peng et al. | |
| 2003/0046983 A1 | 3/2003 | Sato | |
| 2010/0224834 A1 | 9/2010 | Peng et al. | |
| 2011/0098936 A1 | 4/2011 | Bats | |
| 2014/0174152 A1 | 6/2014 | Gil et al. | |

FOREIGN PATENT DOCUMENTS

| | | | | |
|---|---|---|---|---|
| EP | 1265068 | * | 12/2002 | ............ G01N 25/18 |
| EP | 2015056 | | 1/2009 | |
| EP | 2 574 918 | | 4/2013 | |
| JP | 10090033 | | 4/1998 | |
| WO | 9902964 | | 1/1999 | |
| WO | WO-9902964 | * | 1/1999 | ............ G01N 9/26 |
| WO | 2004036209 | | 4/2004 | |

OTHER PUBLICATIONS

Stamps, Douglas, and Sheldon Tieszen. "Blowout of turbulent jet diffusion flames." Fuel 118 (Feb. 15, 2014): 113-122.

Huang, Liji. City natural gas metering. INTECH Open Access Publisher, 2012.

Matter, Daniel et al. "Mikroelektronischer Haushaltsgaszähler mit neuer Technologie" (Micro-electronic household gas meter using new technologies), published in Technisches Messen 71(3) pp. 137-146 (2004).

Olivier Le Corre et al. "Natural gas: physical properties and combustion features", pp. 39-70, <https://www.intechopen.com/books/natural-gas/natural-gas-physical-properties-and-combustion-features>, Aug. 18, 2010.

\* cited by examiner

METHOD AND MEASURING APPARATUS FOR DETERMINING PHYSICAL PROPERTIES OF GAS

RELATED APPLICATIONS

This application is a continuation-in-part (CIP) of U.S. patent application Ser. No. 15/446,783 filed Mar. 1, 2017, which is a continuation of U.S. patent application Ser. No. 14/282,562 filed May 20, 2014, (now U.S. Pat. No. 9,612,229) and claims priority to European Patent Application No. 13002708.9 filed May 24, 2013, the entirety of these applications are incorporated by reference.

BACKGROUND OF INVENTION

The invention relates to a method and a measuring apparatus for determining physical properties and quantities relevant to combustion of gas and gas mixtures. Physical gas properties mean in particular the density, thermal conductivity, heat capacity and viscosity as well as correlatable quantities relevant to combustion, such as the energy content, calorific value, Wobbe index, methane number and/or air requirement of the gas or gas mixture.

In gas-fuel firing control systems it is important to keep the load in the burner constant even at changing fuel gas qualities. The Wobbe index, formed from the calorific value and the root of the density ratio between air and this gas, is the appropriate index for displaying the interchangeability of gases. An identical Wobbe index will then result in a constant thermal load in the burner.

When regulating (natural) gas motors, knowledge of the calorific value at varying (natural) gas qualities is necessary to achieve an increase of performance or efficiency, while for gas the methane number—by analogy to the octane number for gasoline—is used to assess ignition behaviour (knocking effect or misfiring).

An optimal combustion process requires a correct mixing ratio between fuel gas and air—, known as "air requirement". Soot (flue gas) usually forms if there is too little air, and this may damage fuel cells in particular. Too much air during combustion results in reduced performance. The optimal value depends on the application concerned, but changes again with varying gas qualities.

Correlation methods for calculating quantities relevant to combustion have been described in academic literature, see for example U. Wernekinck, "Gasmessung und Gasabrechnung" (Gas metering and gas billing), Vulkan publishers, 2009, ISBN 978-3-8027-5620-7. The following combinations of measured variables are used in this connection:

A. Dielectric constant, sonic velocity, $CO_2$ content
B. Sonic velocity at 2 pressures, $CO_2$ content
C. Thermal conductivity at 2 temperatures, sonic velocity
D. Thermal conductivity, heat capacity, dynamic viscosity
E. Thermal conductivity, infrared absorption (not dispersive)
F. Infrared absorption (dispersive)

There are currently only a few commercially available devices that are approved for calorific value readings, e.g. the EMC500 device by RMG-Honeywell (Type D plus $CO_2$ content) or the Gas-lab Q1 device by Elster-Instromet (Type E plus $CO_2$ content). However, due to the high acquisition costs, none of these devices is suitable for mass distribution.

Integrated CMOS hot-wire anemometers are able to take a microthermal measurement of thermal conductivity as well as of mass flow. For this technology, reference is made to the publication of D. Matter, B. Kramer, T. Kleiner, B. Sabbattini, T. Suter, "Mikroelektronischer Haushaltsgaszähler mit neuer Technologie" (Micro-electronic household gas meter using new technologies), published in Technisches Messen 71, 3 (2004), pp. 137-146. It differs from conventional thermal mass flow meters by taking the measurement directly in the gas flow and not from the outside on a metal capillary tube that encompasses the gas flow.

EP 2 015 056 A1 describes a thermal flow sensor for determining a quantity relevant to combustion, based on a thermal conductivity reading if the mass flow is basically known. A critical nozzle is used to keep the mass flow constant, and the aim is to correct the gas type dependence of the critical nozzle by means of the thermal conductivity. However, the information on the correlation of quantities relevant to combustion is limited to two more or less independent measured variables and thus does not permit validation of the measured data.

WO 2004/036209 A1 describes a sensor for determining a quantity relevant to combustion where the mass flow is kept constant and where a value that is proportional to the heat capacity is identified by means of a thermal measurement. Since the described sensor is not a microthermal sensor, it is not possible to draw conclusions regarding thermal conductivity; this means that the determination of the heat capacity and the quantities relevant to combustion derived therefrom is only possible up to one proportionality factor. As a result, an additional calibration with known gas compositions is required. In addition, the information on thermal conductivity, and thus the means to correlate thermal conductivity $\lambda$ with a quantity relevant to combustion is omitted. Furthermore, the accuracy of this method is limited by the occurring variations of the inaccessible thermal conductivity $\lambda$.

Hence the invention is based on the objective of presenting a method and a measuring apparatus to determine physical properties of gas and gas mixtures in order to achieve a higher degree of accuracy than the sensors from the above referenced patent documents; in addition, the objective is to produce the measuring apparatus at a lower cost than the devices commercially available that are approved for calorific value readings requiring calibration.

The objective is achieved by a method in accordance with certain example embodiments and by a measuring apparatus in accordance with certain example embodiments.

The concept of the invention is to determine physical gas properties, based on measuring the pressure drop of a specified volume of gas through a critical nozzle in combination with a microthermal sensor able to measure the flow as well as thermal conductivity. Both the measurement of the pressure drop and of the flow can be validated for consistency, since the same mass flow for the critical nozzle is also applied to the microthermal sensor.

From these three measured variables it is possible to determine additional values through correlations.

Measuring the Drop in Pressure of a Defined Volume of Gas Using a Critical Nozzle:

The mass flow m through a critical nozzle is described by $$\dot{m} = C_d \cdot p \cdot A^* \cdot \psi_{max} \cdot \sqrt{\frac{M}{T \cdot R_m}}, \quad (1)$$

in which case $C_d$ represents the "discharge coefficient", i.e. the loss factor of an actual critical nozzle compared to an ideal critical nozzle, p the inlet pressure, $A^*$ the nozzle cross-section, T the inlet temperature, $R_m$ the universal gas constant, M the molecular weight of the gas and $\psi_{max}$ the maximum value of the critical flow factor. The latter is a function of the isentropic coefficient $\gamma = c_p/c_V$ (ratio of isobaric to isochoric heat capacity), $$\psi = \sqrt{\gamma} \cdot \left(\frac{\gamma+1}{2}\right)^{\frac{\gamma+1}{2(1-\gamma)}}. \quad (2)$$

If the gas of a known volume V of gas is released from high pressure through the critical nozzle (e.g., from 9 to 4 bar), then according to the ideal gas law, pressure in the volume depends on the time t as follows:

$$p(t) = m(t) \cdot \frac{R_m \cdot T}{M \cdot V}. \quad (3)$$

Therefore, the rate at which the pressure changes results in $$\frac{dp(t)}{dt} = \frac{dm(t)}{dt} \cdot \frac{R_m \cdot T}{M \cdot V} \quad (4)$$
$$= \dot{m}(t) \cdot \frac{R_m \cdot T}{M \cdot V}$$

and together with equation (1) as $$\frac{dp(t)}{dt} = C_d \cdot p \cdot A^* \cdot \psi_{max} \cdot \sqrt{\frac{M}{T \cdot R_m}} \cdot \frac{R_m \cdot T}{M \cdot V} \quad (5)$$
$$= C_d \cdot \frac{A^* \cdot \psi_{max}}{V} \cdot \sqrt{\frac{R_m \cdot T}{M}} \cdot p(t).$$

Accordingly, if the course of the pressure is measured in dependence of the time, then the time constant $\tau$ of the related exponential function obtained by integration can be defined as:

$$1/\tau = \frac{C_d \cdot A^* \cdot \psi_{max}}{V} \cdot \sqrt{\frac{R_m \cdot T}{M}}. \quad (6)$$

If the measuring process additionally delivers the value for temperature T, a gas property factor can be defined by omitting all gas-unrelated variables $$\Gamma^* := C_d \cdot \psi_{max} \cdot \sqrt{\frac{1}{M}}. \quad (7)$$

Equations (3) to (7) are typically used when temperature T is constant. If the gas is released off a known, constant volume V from high pressure through the critical nozzle (e.g., from 9 to 4 bar) and if temperature T is not constant, then according to the ideal gas law, pressure in the volume depends on the time t as follows:

$$\frac{p(t)}{T(t)} = m(t) \cdot \frac{R_m}{M \cdot V}. \quad (3)$$

Therefore, the rate at which the pressure changes is implicitly calculated by taking the time derivative (doted symbols) of both sides of equation (3):

$$\frac{d}{dt}\left(\frac{p(t)}{T(t)}\right) = \frac{\dot{p}T - p\dot{T}}{T^2} \quad (4)$$
$$= \dot{m}(t) \cdot \frac{R_m}{M \cdot V}.$$

For a fast expansion of the gas with negligible heat exchange with the ambience, an isentropic change of state takes place:

$$\frac{T(t)}{T_0} = \left(\frac{p(t)}{p_0}\right)^{\frac{n-1}{n}} \text{ or} \quad (19)$$

$$T(t) = \frac{T_0}{p_0^{(n-1)/n}} \cdot p(t)^{\frac{n-1}{n}} := c \cdot p(t)^{\frac{n-1}{n}} \quad (19.1)$$

with $n = \gamma = c_p/c_V$, $T_0 := T(t_0)$, $p_0 := p(t_0)$, and $t_0$ the time at the beginning of the expansion. Equation (4) can be written as $$\frac{\dot{p} \cdot p^{(n-1)/n} - p \cdot (n-1)/n \cdot p^{-1/n} \cdot \dot{p}}{p^{2(n-1)/n}} = c \cdot \dot{m}(t) \cdot \frac{R_m}{M \cdot V}. \quad (4.1)$$

Inserting the mass flow from equation (1) yields $$\frac{\dot{p} \cdot p^{(n-1)/n} - p \cdot (n-1)/n \cdot p^{-1/n} \cdot \dot{p}}{p^{2(n-1)/n}} = -c \cdot C_d \cdot A^* \cdot \psi_{max} \cdot \sqrt{\frac{M}{T \cdot R_m}} \cdot p \cdot \frac{R_m}{M \cdot V} \quad (5)$$
$$= -C_d \cdot \frac{A^*}{V} \cdot \psi_{max} \cdot \sqrt{\frac{c \cdot R_m}{M}} \cdot p^{(1-n)/2n} \cdot p$$

where the minus sign stands for an outflow of mass. Simplifying equation (5) by sorting all pressure terms to the left side and separating variables results in a differential equation for p, which can then be integrated:

$$\int_{p_0}^{p(t)} p^{(1-3n)/2n} \cdot dp = -n \cdot C_d \cdot \frac{A^*}{V} \cdot \psi_{max} \cdot \sqrt{\frac{c \cdot R_m}{M}} \cdot \int_{t_0}^{t} dt. \quad (5.1)$$

Pressure p(t) follows directly from the integration on both sides of equation (5.1):

$$p^{(1-n)/2n}\Big|_{p_0}^{p} = -\frac{1-n}{2} \cdot C_d \cdot \frac{A^*}{V} \cdot \psi_{max} \cdot \sqrt{\frac{c \cdot R_m}{M}} \cdot (t - t_0). \quad (5.2)$$

Inserting c from equation (19.1) and dividing both sides by $p_0^{(1-n)/2n}$ gives then the expression for p(t):

$$\frac{p(t)}{p_0} = \left( \frac{n-1}{2} \cdot C_d \cdot \frac{A^*}{V} \cdot \psi_{max} \cdot \sqrt{\frac{T_0 \cdot R_m}{M}} \cdot (t-t_0) + 1 \right)^{2n/(1-n)}, \quad (5.3)$$

which can also be written as $$\frac{p(t)}{p_0} = \left( \frac{n-1}{2} \cdot \frac{(t-t_0)}{\tau} + 1 \right)^{2n/(1-n)} \quad (5.4)$$

with time constant $\tau$ being a function of gas properties and the initial temperature $T_0$:

$$1/\tau = C_d \cdot \frac{A^*}{V} \cdot \psi_{max} \cdot \sqrt{\frac{T_0 \cdot R_m}{M}}. \quad (6)$$

If the measuring process additionally delivers the value for temperature $T_0$, a gas property factor can be determined defined by omitting all gas-unrelated variables:

$$\Gamma^* := C_d \cdot \psi_{max} \cdot \sqrt{\frac{1}{M}}. \quad (7)$$

n=γ represents the isentropic case in general. For n→1, the isothermal case follows, which is easily seen from equation (19), i.e. $T(t)/T_0=1$, meaning that $T(t)=T_0$, i.e. T=constant. In this case, equation (5) converges into equation (5).

Depending on the amount of heat exchange between gases in a gas reservoir with volume V and the walls of the reservoir, n is within $1 \leq n \leq \gamma$. Since n, called the polytropic index, is a second parameter besides $\tau$ in equation (5.4), a fit to measured pressure decay curves reveals not only $\Gamma^*$ in equation (7), but also additional information via the fit results for n. This can be seen by studying the isentropic or adiabatic case, where $n=\gamma=c_p/c_V$ of the measured gas. For a mono-atomic gas (e.g. argon), γ=5/3, while for a diatomic gas such as air γ=7/5. For molecules with more than two atoms, γ=8/6. Therefore, n can be used to discriminate gas species that otherwise are not distinguishable by the gas property factor $\Gamma^*$. E.g. argon and ethane (and any mixture of them) have the same $\Gamma^*$ to within 2.5% at room temperature, but differ completely in their combustion properties. In contrast, n=1.67 for argon while n=1.18 for ethane, i.e. it is easily distinguishable, whether the gas is combustible or not.

In general, $1 \leq n \leq \gamma$ holds. The adiabatic case described above suggests a dependency of n on the gas species also in the case n<γ. This means, n provides additional information on the gas properties, except for the isothermal case, where n=const.=1.

The design of a measuring apparatus determines whether n is closer to the isothermal or adiabatic case by means of heat exchange between the gas reservoir and the gas therein. Constant temperature is best implemented in a set-up with many cooling (or heating) fins, e.g. a passel of small holes or fine flow channels that transport heat fast into or out of the gas. In contrast, the adiabatic case with perfect heat insulation is best approximated by an insulated hollow sphere with lowest surface to volume ratio. An insulated hollow sphere is difficult to implement in practice. An easy to drill cylindrical hole is an alternative choice.

FIG. 11 shows pressure decay curves calculated for different polytropic indices with pressure being displayed on a logarithmic ordinate.

Conversely, if the gas is released from a higher pressure level through the critical nozzle into a known volume V (e.g., from ambient pressure to vacuum), the equation (5') for the pressure increase in volume V reads as follows:

$$\frac{dp(t)}{dt} = C_d \cdot p_{Nozzle} \cdot A^* \cdot \psi_{max} \cdot \sqrt{\frac{M}{T \cdot R_m}} \cdot \frac{R_m \cdot T}{M \cdot V}, \quad (5')$$

$$= C_d \cdot \frac{A^* \cdot \psi_{max}}{V} \cdot \sqrt{\frac{R_m \cdot T}{M}} \cdot p_{Nozzle}$$

in which case the pressure before the nozzle $p_{nozzle}$ remains constant, which leads over time to a linear pressure increase in volume V with $$\frac{C_d \cdot A^* \cdot \psi_{max}}{V} \cdot \sqrt{\frac{R_m \cdot T}{M}} \cdot p_{Nozzle} \quad (6')$$

being a proportionality constant. If, in addition, the values of the temperature T and the nozzle inlet pressure $p_{Nozzle}$ are obtained by the measurement, it is possible to define in turn the gas property factor $$\Gamma^* := C_d \cdot \psi_{max} \cdot \sqrt{\frac{1}{M}} \quad (7')$$

by omitting all gas-unrelated variables.

Equations (5') to (7') are typically used when temperature T is considered constant. If the gas is released from a higher pressure level through the critical nozzle into a known volume V (e.g., from ambient pressure to vacuum) and if temperature T is not constant, the equation (5') for the pressure increase in volume V (plus sign for mass inflow) reads as follows:

$$\dot{p} \cdot p^{(n-1)/n} - p \cdot \quad (5')$$

$$\frac{(n-1)/n \cdot p^{-1/n} \cdot \dot{p}}{p^{2(n-1)/n}} = +c \cdot C_d \cdot A^* \cdot \psi_{max} \cdot \sqrt{\frac{M}{T \cdot R_m}} \cdot p_{nozzle} \cdot \frac{R_m}{M \cdot V}$$

$$= C_d \cdot \frac{A^*}{V} \cdot \psi_{max} \cdot \sqrt{\frac{c \cdot R_m}{M}} \cdot p_{nozzle} \cdot p^{(1-n)/2n}$$

in which case the pressure before the nozzle $p_{nozzle}$ remains constant.

Following the same procedure of integration as above yields p(t):

$$\frac{p(t)}{p_0} = \left( \frac{n+1}{2} \cdot C_d \cdot \frac{A^*}{V} \cdot \psi_{max} \cdot \sqrt{\frac{T_0 \cdot R_m}{M}} \cdot (t-t_0) \frac{p_{nozzle}}{p_0} + 1 \right)^{2n/(1+n)}, \quad (5.3')$$

which can also be written as $$\frac{p(t)}{p_0} = \left(\frac{n+1}{2} \cdot \frac{(t-t_0)}{\tau} + 1\right)^{2n/(1+n)} \quad (5.4')$$

with time constant $\tau$ being a function of gas properties, the initial temperature and pressure $T_0$ and $p_0$, respectively, and the pressure before the nozzle $p_{nozzle}$:

$$1/\tau = C_d \cdot \frac{A^*}{V} \cdot \psi_{max} \cdot \sqrt{\frac{T_0 \cdot R_m}{M}} \frac{p_{nozzle}}{p_0}. \quad (6')$$

If, in addition, the values of the temperature $T_0$, $p_0$ and the nozzle inlet pressure $p_{nozzle}$ are obtained through the measurement, it is possible to define in turn the gas property factor $$\Gamma^* := C_d \cdot \psi_{max} \cdot \sqrt{\frac{1}{M}}. \quad (7')$$

by omitting all gas-unrelated variables.

For $n \to 1$ (isothermal case), equation (5.4') reads simply as $$\frac{p(t)}{p_0} = \frac{t-t_0}{\tau} + 1 \quad (5.4'')$$

which is a linear time increase in pressure with proportionality factor $1/\tau$ from equation (6').

Mass Flow Measurement by Means of a Microthermal Sensor:

The starting point for describing the microthermal mass flow measurement is that of the one-dimensional thermal conductivity equation describing the microthermal system (Kerson Huang: *Statistical Mechanics,* 2nd volume, John Wiley & Sons, New York 1987, ISBN 0-471-85913-3):

$$\frac{c_p}{\lambda} \cdot \rho v_x \cdot \frac{d}{dx} T = \nabla^2 T + \frac{1}{\lambda} \Theta, \quad (8)$$

in which
$v_x$ represents the component of the mean flow rate (velocity vector) $\vec{v}$ in the direction of x, i.e. in the direction of the gas flow,
T represents temperature, $$\frac{d}{dx} T$$

represents the temperature gradient,
$c_p$ represents the heat capacity of the gas at constant pressure,
$\rho$ represents density,
$\lambda$ represents the thermal conductivity of the gas,
$\nabla^2 T$ represents the Laplacian operator, applied to temperature T, in which $$\nabla^2 = \left(\frac{d}{d_x}\right)^2 + \left(\frac{d}{dy}\right)^2 + \left(\frac{d}{dz}\right)^2.$$

Since the gas (gas flow) flows only in the direction x, the components $v_y$ and $v_z$ in direction y, respectively direction z of the mean flow rate $\vec{v}$ are taken to be zero. $\Theta$ with the unit Watt/m³ describes the source term of the heat element. In the microthermal method, the source term is the heating wire of a miniaturised, integrated hot-wire anemometer, which feeds thermal energy into the system. From the solution of equation (8), which describes the temperature distribution in the microthermal system, it is possible, by measuring this temperature distribution, to determine the factor S, $$S := \frac{c_p}{\lambda} \cdot \rho \cdot v_x = \frac{c_p}{\lambda} \cdot \frac{\dot{m}}{A}, \quad (9)$$

wherein A means the cross-section of the flow channel past the microthermal sensor. In combination with the critical nozzle, i.e. by arranging the microthermal sensor after the critical nozzle, the mass flow is provided by equation (1), therefore by $$\frac{c_p}{\lambda} \cdot \rho \cdot v_x = \frac{c_p}{\lambda} \cdot C_d \cdot p \cdot \frac{A^*}{A} \cdot \psi_{max} \cdot \sqrt{\frac{M}{T \cdot R_m}}. \quad (10)$$

Measuring pressure p and temperature T, and omitting again all gas-unrelated variables, delivers a second gas property factor $$\Gamma = \frac{c_p}{\lambda} \cdot C_d \cdot \psi_{max} \cdot \sqrt{M}. \quad (11)$$

The omission of all gas-unrelated variables in equation (7) and equation (11) is done implicitly, by putting $\Gamma$ and $\Gamma^*$ in relation to $\Gamma$ und $\Gamma^*$ of a known (calibration) gas. See also FIG. 4.

Measuring Thermal Conductivity by Means of Microthermal Sensor:

It should be noted that the thermal conductivity $\lambda$, due to the source term $\Theta$, has an additional, separate impact on the solution of equation (8). The same applies in reverse: the thermal conductivity can be determined if the microthermal sensor is measured without an applied mass flow ($v_x=0$ or $\dot{m}=0$). The related differential equation for temperature distribution then simply reads $$\nabla^2 T = -\frac{1}{\lambda} \Theta. \quad (12)$$

Validation of the Gas Property Factors $\Gamma$ or $\Gamma^*$:

The ratio of the two gas property factors $\Gamma$ and $\Gamma^*$ results in $$\Gamma/\Gamma^* = \frac{c_p}{\lambda} \cdot M \propto \frac{c_p}{\lambda} \cdot \rho_{norm}, \quad (13)$$

since the molecular weight is proportional to the standard density (density at standard conditions 1013.25 mbar and 273.15 K), due to the fact that for most gases, the mol volume is almost identical. Thus, in equation (9), the flow rate $v_x$ and, in conjunction with the flow channel cross-section A, the standard volume flow $\phi_{norm}=v_x \cdot A$ can be extracted from the factor S, measured with the microthermal sensor. The integration of this volume flow over time, i.e. the time interval $t_2-t_1$, should then correspond with the released gas volume calculated on the basis of the corresponding pressure and temperature values:

$$\int_{t_1}^{t_2} \phi_{norm}(t)dt \stackrel{!}{=} \frac{(p(t_2)-p(t_1))}{1013.25 \text{ mbar}} \cdot \frac{273.15 \text{ } K}{T} \cdot V. \quad (14)$$

If these two values do not match, the standard volume flow or the pressure signal can be adjusted, depending on which value can be measured less accurately, to the point that equation (14) is satisfied. In the case of a standard volume flow adjustment for $v_x=\phi_{norm}/A$, the right side of the equation (13) is also adjusted through the measured factor S in equation (9), and thus also the gas property factor Γ, again by aid of equation (13). In the case of a pressure signal adjustment, the time constant r in equation (6), respectively the proportionality constant in equation (6'), is adjusted, which in turn leads to an adjustment of the gas property factor Γ* in equation (7) or (7'). In this way, Γ and Γ* have been defined consistently, because the mass flow through the nozzle is the same as the mass flow with which the microthermal sensor is supplied.

Correlation of Quantities Relevant to Combustion:

By measuring the gas property factors Γ and Γ* as well as thermal conductivity λ, three independent measured variables are obtained, with which it is now possible to correlate quantities relevant to combustion Q by aid of a function $f_{corr}$:

$$Q_{corr}=f_{corr}(\Gamma,\Gamma^*,\lambda). \quad (15)$$

For example, for correlating the density ratio $\rho_{corr}/\rho_{ref}$ at 0° C. and 1013.25 mbar, as shown in FIG. 4, the following correlation function $$\rho_{corr}/\rho_{ref}=f_{corr}(\Gamma,\Gamma^*,\lambda)=\Gamma^r \cdot \Gamma^{*s} \cdot \lambda^t \quad (16)$$

is obtained, with exponents r=−0.2, s=−1.8 and t=−0.2 and a typical H-gas used for reference purposes.

Equation (15) and (16) are typically used when temperature T is constant. In the polytropic case when temperature T is not constant, four independent, measured variables can be obtained by measuring the gas property factors Γ and Γ* as well as thermal conductivity λ and the polytropic index n. With the four independent variables it is now possible to correlate quantities relevant to combustion Q by aid of a function $f_{corr}$:

$$Q_{corr}=f_{corr}(\Gamma,\Gamma^*,\lambda,n) \quad (15)$$

which can e.g. read as follows:

$$Q_{corr}=f_{corr}(\Gamma,\Gamma^*,\lambda,n)=\text{const} \cdot \Gamma^r \cdot \Gamma^{*s} \cdot \lambda^t \cdot n^u \quad (16)$$

with r, s, t and u being exponents, and const being a constant.

SUMMARY OF INVENTION

In the method for determining physical properties and/or quantities relevant to combustion of gas and gas mixtures according to the present invention:

the gas or gas mixture flows from a gas reservoir through a critical nozzle and past a microthermal sensor, with the same mass flow being applied to the critical nozzle and the microthermal sensor;

the pressure drop in the gas reservoir is measured as a function of time;

a first gas property factor Γ*, dependent on a first group of physical properties of the gas or gas mixture, is determined on the basis of the measured values of the pressure drop, with the first gas property factor being derived, for example, from a time constant of the pressure drop;

a second gas property factor Γ, dependent on a second group of physical properties of the gas or gas mixture, is determined by the flow signal of the microthermal sensor, with the second gas property factor containing, for example, the heat capacity $c_p$ of the gas or gas mixture, or being dependent on the same;

the thermal conductivity λ of the gas or gas mixture is determined with the aid of the microthermal sensor; and a desired physical property or quantity relevant to combustion is determined by the first and/or second gas property factor Γ*, Γ and thermal conductivity λ through correlation.

The method is advantageously based on an exponential decline of the measured pressure and derives the first gas property factor Γ* from the time constant of the pressure drop, in which case the first gas property factor is formed, for example, by measuring additionally temperature T and by omitting all gas-unrelated variables.

The second gas property factor (Γ) typically contains the quotient of the heat capacity $c_p$, divided by the thermal conductivity λ of the gas or gas mixture, or is dependent on the same, with the second gas property factor being formed by measuring in addition, for example, the temperature T and by omitting all gas-unrelated variables.

According to an advantageous embodiment of the method, the gas property factors Γ*, Γ are validated by comparing the values for the total volume of the released gas or gas mixture; this is done by measuring the pressure and temperature in the gas reservoir at the start and the end of the pressure drop reading and by determining the released standard volume at a known volume of the gas reservoir, by accumulating the standard flow measured with the microthermal sensor across the time interval between the start and end of the pressure drop reading, and by comparing the released standard volume to the accumulated standard flow. In case of a discrepancy, the first and/or the second gas property factor is adjusted, e.g. by adjusting the pressure signal or the standard flow value of the microthermal sensor.

The embodiment of the method described above can be used to calibrate the flow signal of the microthermal sensor by calibrating the flow signal of the microthermal sensor for a specific calibration gas or gas mixture, by determining the ratio Γ/Γ* of the second gas property factor, derived from the flow signal of the microthermal sensor, to the first gas property factor for an unknown gas or gas mixture, and by comparing the standard volume values from the pressure drop reading and the accumulated standard flow of the microthermal sensor, and to use them to adjust the ratio of the second gas property factor to the first and to adapt the value for the second gas property factor Γ.

In a further advantageous embodiment of the method for determining physical properties and/or quantities relevant to combustion of the gas or gas mixture:

the gas or gas mixture flows under pressure through a critical nozzle and past a microthermal sensor into a gas reservoir, with the same mass flow being applied to the critical nozzle and the microthermal sensor;

the pressure increase in the gas reservoir is measured as a function of time;

a first gas property factor $\Gamma^*$, dependent on a first group of physical properties of the gas or gas mixture, is determined by reference to the measured variables of the pressure increase;

a second gas property factor $\Gamma$, dependent on a second group of physical properties of the gas or gas mixture, is determined from the flow signal of the microthermal sensor, with the second gas property factor containing, for example, the heat capacity $c_p$ of the gas or gas mixture, or being dependent on the same;

the thermal conductivity $\lambda$ of the gas or gas mixture is determined with the aid of the microthermal sensor; and a desired physical property or quantity relevant to combustion is determined from the first and/or second gas property factor $\Gamma^*$, $\Gamma$ and thermal conductivity $\lambda$ through correlation.

The method is advantageously based on a linear increase of the measured pressure and derives the first gas property factor $\Gamma^*$ from the proportionality constant of the pressure increase, in which case the first gas property factor is formed, for example, by measuring additionally the temperature T and the nozzle inlet pressure $p_{Nozzle}$ and by omitting all gas-unrelated variables.

The second gas property factor $\Gamma$ typically contains the quotient of the heat capacity $c_p$ divided by the thermal conductivity $\lambda$ of the gas or gas mixture or is dependent on the same, in which case the second gas property factor is formed, for example, by measuring additionally the temperature T and by omitting all gas-unrelated variables.

According to a further advantageous embodiment of the method, the gas property factors $\Gamma^*$, $\Gamma$ are validated by comparing the values for the total volume of the gas or gas mixture flown into the gas reservoir; this is done by measuring the pressure and temperature in the gas reservoir at the start and end of the pressure increase reading and by determining the standard volume fed into the gas reservoir at a known volume of the gas reservoir, by accumulating the standard flow measured with the microthermal sensor across the time interval between the start and end of the pressure increase reading, and by comparing the standard volume fed into the gas reservoir to the accumulated standard flow. In case of a discrepancy, the first and/or the second gas property factor is adjusted, e.g. by adjusting the pressure signal or the standard flow value of the microthermal sensor.

The embodiment of the method described above can be used to calibrate the flow signal of the microthermal sensor by calibrating the flow signal of the microthermal sensor for a specific calibration gas or gas mixture, by determining the ratio $\Gamma/\Gamma^*$ of the second gas property factor, derived from the flow signal of the microthermal sensor, to the first gas property factor for an unknown gas or gas mixture, and by comparing the standard volume values from the pressure increase reading and the accumulated standard flow of the microthermal sensor, and to use them to adjust the ratio of the second gas property factor to the first and to adapt the value for the second gas property factor $\Gamma$.

The desired physical property may be, for example, the density or the thermal conductivity or the heat capacity or the viscosity of the gas or gas mixture, and the quantity relevant to combustion may be, for example, the energy content or the calorific value or the Wobbe index or the methane number or the air requirement of the gas or gas mixture.

The desired physical property or quantity relevant to combustion Q is determined advantageously by aid of a correlation function $Q=f_{corr}(\Gamma, \Gamma^*, \lambda)=\text{const}\cdot\Gamma^r\cdot\Gamma^{*s}\cdot\lambda^t$, wherein r, s and t are exponents, and const is a constant.

The pressure in the gas reservoir at the start of the pressure drop measurement is typically higher than the critical pressure $p_{crit}$ of the critical nozzle and the external pressure downstream of the critical nozzle is less than half the critical pressure, or the pressure in the gas reservoir at the start of the pressure increase reading is typically less than half the critical pressure $p_{crit}$ of the critical nozzle and the pressure upstream of the critical nozzle is higher than the critical pressure.

The gas reservoir is typically disconnected from the gas supply during the measurement, irrespective of the embodiment and variant. The volume of the gas reservoir can be selected advantageously in such a way that the pressure inside the gas reservoir significantly decreases or increases by the end of the measurement, for example, by at least a tenth or a fifth of the initial pressure.

The measuring apparatus for determining physical properties and/or quantities relevant to combustion of a gas or gas mixture according to the present invention includes an analyzer unit that is configured to carry out a procedure in accordance with one of the embodiments or variants described above, as well as a gas reservoir, that is equipped with a pressure sensor, a critical nozzle and a microthermal sensor to measure the flow and thermal conductivity. In this set-up the gas reservoir is connected to the critical nozzle and the microthermal sensor for the purposes of measuring.

Furthermore, the invention also includes the use of a gas reservoir and a critical nozzle to determine physical properties and/or quantities relevant to combustion of a gas or gas mixture; in this set-up the gas or gas mixture flows under pressure from the gas reservoir through the critical nozzle, and the pressure drop in the gas reservoir is measured as a function of time, a gas property factor $\Gamma^*$, dependant on the physical properties of the gas or gas mixture is determined on the basis of the measured values of the pressure drop, derived, for example, from a time constant of the pressure drop; the gas property factor $\Gamma^*$ then serves to determine a desired physical property or quantity relevant to combustion through correlation.

In another advantageous embodiment, low pressure is generated in the reservoir, and the gas or gas mixture flows under pressure through the critical into the gas reservoir; in this set-up, the pressure increase in the gas reservoir is measured as a function of time, and a gas property factor $\Gamma^*$, dependent on the physical properties of the gas or gas mixture, is determined from the measured values of the pressure increase, which then serves to determine a desired physical property or quantities relevant to combustion through correlation.

The above-described use of a gas reservoir and a critical nozzle to determine physical properties and/or quantities relevant to combustion of a gas or gas mixture, or the corresponding method in which a gas reservoir and a critical nozzle are used for determining physical properties and/or quantities relevant to combustion of a gas or gas mixture, can also be seen as a distinct, independent invention, which may additionally include a measuring apparatus with an analyzer unit, a gas reservoir and a critical nozzle, in which case the analyzer unit is configured for the use of the gas reservoir and the critical nozzle to determine physical properties and/or quantities relevant to combustion of a gas or gas mixture or to carry out the corresponding method.

In addition, the invention encompasses the use of a gas reservoir and a microthermal sensor calibrated for a specific calibration gas or gas mixtures to determine physical properties and/or quantities relevant to combustion of gas or gas mixtures; in this set-up the gas or gas mixture flows under pressure from the gas reservoir past the microthermal sensor, in which case the volume flow $v_x \cdot A$, determined by the microthermal sensor calibrated for a specific calibration gas or gas mixture, is accumulated and compared to the gas volume released from the gas reservoir; from the comparison of the two volumes a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v'_x = c_p \cdot \rho / \lambda$ (see equation (9)), through correlation.

In another advantageous embodiment, low pressure is generated in the gas reservoir, and the gas or gas mixtures flows under pressure past the microthermal sensor into the gas reservoir, in which case the volume flow $v_x \cdot A$, determined by the microthermal sensor calibrated for a specific calibration gas or gas mixture, is accumulated and compared to the gas volume flowing into the gas reservoir; from the comparison of the two volumes a gas property factor $S/v'_x$, dependent on the physical properties of the gas or gas mixture, is determined, and in which the desired physical property or quantity relevant to combustion is determined from the gas property factor, which may be represented, for example, by $S/v'_x = c_p \cdot \rho / \lambda$ (see equation (9)), through correlation.

In another advantageous variant of the embodiment, the gas flow is generated by moving a piston.

The above-described use of a gas reservoir and a microthermal sensor calibrated for a specific calibration gas or gas mixture to determine physical properties and/or quantities relevant to combustion of a gas or gas mixture, or the corresponding method, in which a gas reservoir and a microthermal sensor calibrated for a specific calibration gas or gas mixture are used to determine physical properties and/or quantities relevant to combustion of gas or a gas mixture, can also be seen as a distinct, independent invention, which may additionally comprise a measuring apparatus with an analyzer unit, a gas reservoir and a microthermal sensor, in which case the analyzer unit is configured for the use of the gas reservoir and the microthermal sensor to determine physical properties and/or quantities relevant to combustion of a gas or gas mixture or to carry out the corresponding method.

The invention can also be described as follows:

A method for determining physical properties and/or quantities relevant to combustion of gas and/or gas mixtures, the method comprising: flowing a gas or gas mixture from a gas reservoir or into a gas reservoir with the gas or gas mixture flowing under pressure through a critical nozzle and past a microthermal sensor, wherein the same mass flow is applied to the critical nozzle and the microthermal sensor; measuring pressure drop or pressure increase respectively in the gas reservoir as a function of time; determining a first gas property factor $\Gamma^*$, which is dependent on a first group of physical properties of the gas and/or gas mixture, on the basis of measured values of the pressure drop or pressure increase determining a second gas property factor $\Gamma$, which is dependent on a second group of physical properties of the gas or gas mixture, from a flow signal generated by the microthermal sensor; determining the thermal conductivity $\lambda$ of the gas and/or gas mixture using the microthermal sensor; and determining a physical property and/or quantity relevant to combustion from the first and/or second gas property factor $\Gamma^*$, $\Gamma$ and the thermal conductivity $\lambda$ through correlation.

The feature "measuring pressure drop or pressure increase respectively in the gas reservoir as a function of time" can e.g. mean that pressure is measured in the gas reservoir at least three, four, five or more times. Typically, the number of pressure measurements in the gas reservoir is a multiple of that.

In an advantageous variant of the method, the starting point is an exponential decline of the measured pressure and the first gas property factor $\Gamma^*$ is derived from the time constant of the pressure drop, or the starting point is a linear increase of the measured pressure and the first gas property factor $\Gamma^*$ is derived from a proportionality constant of the pressure increase.

In another advantageous variant the starting point is an adiabatic decline or increase of the measured pressure and the first gas property factor $\Gamma^*$ is derived from a polytropic index n of the gas or gas mixture and/or a time constant of the pressure drop or pressure increase respectively.

In still another advantageous variant the second gas property factor $\Gamma$ contains the quotient of heat capacity $c_p$ divided by thermal conductivity $\lambda$ of the gas or gas mixture, or is dependent on the same.

The first and/or the second gas property factor are typically formed by measuring the nozzle inlet pressure $p_{Nozzle}$ and/or the temperature T or initial temperature $T_0$ and by omitting all gas-unrelated variables.

In an advantageous embodiment of the method described above the gas property factors $\Gamma^*$, $\Gamma$ are validated by comparing the values for the total volume of the gas or gas mixture released from or fed into the gas reservoir by: measuring the pressure and temperature in the gas reservoir at the start and end of the pressure drop or pressure increase reading and by determining the standard volume released or fed respectively by reference to the known volume of the gas reservoir; summing up the standard flow measured with the microthermal sensor during the time interval between the start and end of the pressure drop or pressure increase reading; comparing the standard volume released or fed respectively to the summed up standard volume; and in case of a discrepancy, by adjusting the first and/or the second gas property factor $\Gamma^*$, $\Gamma$ and/or by adjusting the pressure signal and/or the standard flow variable of the microthermal sensor.

In another advantageous embodiment the method described above is used for calibrating the flow signal of the microthermal sensor, by: calibrating the flow signal of the microthermal sensor for a specific calibration gas or gas mixture; determining the ratio $\Gamma/\Gamma^*$ of the second gas property factor, determined on the basis of the flow signal of the microthermal sensor, to the first gas property factor for an unknown gas or gas mixture; and comparing the standard volume values from the reading of the pressure drop or pressure increase and the reading of the summed up standard flow of the microthermal sensor, which are then used to adjust the ratio of the second gas property factor to the first, and to adapt the value for the second gas property factor $\Gamma$.

The desired physical property can e.g. be the density or the thermal conductivity or the heat capacity or the viscosity of the gas or gas mixture, and/or the quantity relevant to combustion can e.g. be the energy content or the calorific value or the Wobbe index or the methane number or the air requirement of the gas or gas mixture.

In a further advantageous variant of the method described above, the polytropic index (n) is determined on the basis of measured values of the pressure drop or pressure increase respectively, and/or the first and/or second gas property factor Γ*, Γ, the thermal conductivity λ and the polytropic index n is used to determine a physical property and/or quantity relevant to combustion through correlation.

The desired physical property or the quantity relevant to combustion Q can e.g. be determined by aid of a correlation function $$Q=f_{corr}(\Gamma,\Gamma^*,\lambda)=const \cdot \Gamma^r \cdot \Gamma^{*s} \cdot \lambda^t \text{ or}$$

$$Q=f_{corr}(\Gamma,\Gamma^*,\lambda,n)=const \cdot \Gamma^r \cdot \Gamma^{*s} \cdot \lambda^t \cdot n^u,$$

wherein r, s, t and u are exponents, and const is a constant.

In a second embodiment of the invention, a method to use a gas reservoir and a critical nozzle for determining physical properties and/or quantities relevant to combustion of gas or gas mixtures comprises: flowing a gas or gas mixture from the gas reservoir or into the gas reservoir with the gas or gas mixture flowing under pressure through the critical nozzle; measuring the pressure drop or pressure increase respectively in the gas reservoir as a function of time; determining a gas property factor Γ*, which is dependent on the physical properties of the gas or gas mixture, on the basis of measured values of the pressure drop or pressure increase; and determining a desired physical property or quantity relevant to combustion on the basis of the gas property factor Γ* through correlation.

In an advantageous embodiment variant, the starting point is an exponential decline of the measured pressure and the gas property factor Γ* is derived from the time constant of the pressure drop, or the starting point is a linear increase of the measured pressure and the gas property factor Γ* is derived from a proportionality constant of the pressure increase.

In another advantageous embodiment variant, the starting point is an adiabatic decline or increase of the measured pressure and the first gas property factor Γ* is derived from a polytropic index n of the gas or gas mixture and/or a time constant of the pressure drop or pressure increase respectively.

In still another advantageous embodiment variant, the first and/or the second gas property factor is formed by measuring the nozzle inlet pressure $p_{Nozzle}$ and/or the temperature T or initial temperature $T_0$ and by omitting all gas-unrelated variables.

In still another advantageous embodiment variant, the polytropic index (n) is determined on the basis of measured values of the pressure drop or pressure increase respectively, and/or the first and/or second gas property factor Γ*, Γ, the thermal conductivity λ and the polytropic index n are used to determine a physical property and/or quantity relevant to combustion through correlation.

In a third embodiment of the invention, a method to use a gas reservoir and a microthermal sensor to determine physical properties and/or quantities relevant to combustion of gas or gas mixtures comprises: flowing a gas or gas mixture from the gas reservoir or into the gas reservoir with the gas or gas mixture flowing under pressure past the microthermal sensor; determining a flow rate $v_x$ of the gas or gas mixture using the microthermal sensor; determining a summed-up volume flow $v_x \cdot A$ based on the flow rate $v_x$; comparing the summed up volume flow to the gas volume released from or fed into the gas reservoir; determining a gas property factor $S/v'_x$, dependent on the physical properties of the gas or gas mixture, on the basis of the comparison of the two volumes, wherein the quantity $v'_x$ represents the flow rate calculated on the basis of the gas volume released from or fed into the gas reservoir respectively; and determining a desired physical property or quantity relevant to combustion on the basis of the gas property factor through correlation.

In an advantageous embodiment of the method, the thermal conductivity λ of the gas or gas mixture is determined with the aid of the microthermal sensor, and/or the desired physical property or quantity relevant to combustion is determined on the basis of the gas property factor and the thermal conductivity λ through correlation.

In an advantageous embodiment variant, a classification of the measured gas as H-gas or L-gas is made with the aid of the thermal conductivity λ in conjunction with the gas property factor, and/or the gas property factor is defined as: $S/v'_x = c_p \cdot \rho / \lambda$.

In addition, the invention comprises a measuring apparatus for determining physical properties and/or quantities relevant to combustion of gas or gas mixtures with the measuring apparatus comprising: an analyzer unit that is configured to carry out a method in accordance with one of the above described embodiments and embodiment variants, a gas reservoir that is equipped with a pressure sensor, and a critical nozzle and/or a microthermal sensor to measure the flow and thermal conductivity.

In an advantageous variant, the measuring apparatus comprises a compressor to increase the pressure in the gas reservoir or a vacuum pump to generate low pressure in the gas reservoir.

In an advantageous embodiment of the measuring apparatus, the gas reservoir is equipped with a heat exchanger or heat exchanging means to approximate isothermal conditions or with a heat insulation to limit heat exchange in the adiabatic or near adiabatic case.

The advantage of the method and measuring apparatus to determine physical properties and/or quantities relevant to combustion of a gas or gas mixture pursuant to the present invention is that three independent measured variables are available for correlating quantities relevant to combustion. This makes it possible, on the one hand, to achieve a comparatively high level of accuracy for determining quantities relevant to combustion, which otherwise can only be achieved with substantially more expensive devices; on the other hand, it is possible to validate the readings and to adjust any deviations.

Other advantages are apparent from the following specification.

SUMMARY OF DRAWINGS

The invention is explained in more detail below with reference to the drawings. In the drawings.

DETAILED DESCRIPTION

Figure 1A:
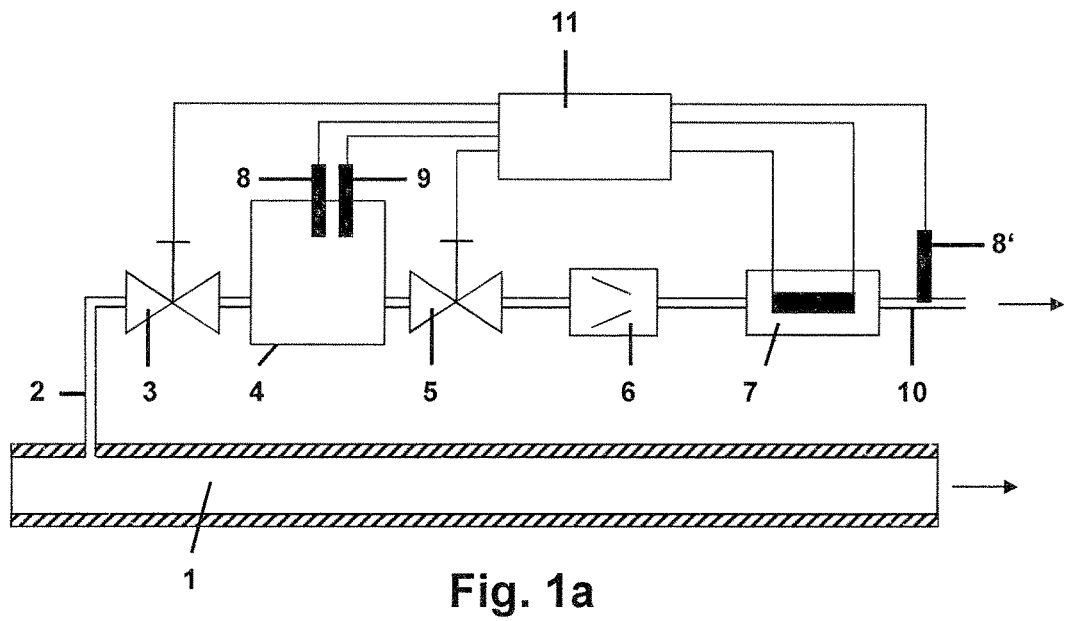
FIG. 1a shows an exemplary embodiment of a schematic configuration of a measuring apparatus according to the present invention (high-pressure variant)

FIG. 1a shows an exemplary embodiment of a schematic configuration of a measuring apparatus according to the present invention in which the pressure in the main gas duct 1 is higher than the critical pressure for the critical nozzle 6 of the measuring apparatus (high-pressure variation). In the exemplary embodiment, the measuring apparatus consists, in addition to the critical nozzle 6, of an analyzer unit 11, which is configured for performing the method according to the present invention, a gas reservoir 4, which is equipped with a pressure sensor 8 and a microthermal sensor 7 to measure the flow and thermal conductivity, in which case the gas reservoir 4 is connected with the critical nozzle 6 and the microthermal sensor 7 for the measurements.

If required, the measuring apparatus may comprise one or more of the following additional components: a test line 2, which leads to the gas reservoir 4, and which may be connected to a main gas duct 1 during operation, an inlet valve 3, which may be arranged in the test line 2 to control the gas supply to the gas reservoir, an outlet valve 5, installed on the outlet side of the gas reservoir to control the flow of gas from the gas reservoir, an outlet 10 for discharging the gas released from the measuring apparatus, an additional pressure sensor 8', which may be installed on the outlet 10, a temperature sensor 9, which is installed in the gas reservoir, and a compressor 12', which may be installed on the inlet side of the gas reservoir 4 to increase the pressure in the gas reservoir.

An exemplary embodiment of the method for determining physical properties and/or quantities relevant to combustion of gas or gas mixtures according to the present invention is described below with reference to FIG. 1a. In this method, the gas or gas mixture flows from a gas reservoir 4 through a critical nozzle 6 and past a microthermal sensor 7, with the same mass flow being applied to the critical nozzle and the microthermal sensor. The pressure drop in gas reservoir 4 is measured as a function of time and a first gas property factor $\Gamma^*$, dependent on a first group of physical properties of the gas or gas mixture, is determined on the basis of the measured values of the pressure drop, with the first gas property factor being derived, for example, from a time constant of the pressure drop. A second gas property factor $\Gamma$, dependent on a second group of physical properties of the gas or gas mixture, is calculated from the flow signal of the microthermal sensor 7, with the second gas property factor including, for example, the heat capacity $c_p$ of the gas or gas mixture, or being dependent on the same. Next, the thermal conductivity $\lambda$ of the gas or gas mixture is determined with the aid of the microthermal sensor 7, and the desired physical property or quantity relevant to combustion is determined by aid of correlation on the basis of the first and/or second gas property factor $\Gamma^*$, $\Gamma$ and the thermal conductivity.

Other advantageous embodiments and variants of the method are described in the preceding sections of the specification. The following description provides additional details on the method that may be used if desired.

Advantageously, the inlet valve 3 and the outlet valve 5 are opened first to allow the gas or gas mixture that is to be measured to flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 1a. In this case, the outlet valve 5 closes and the gas reservoir 4, the volume content V of which is known, fills up until the inlet valve 3 is closed. Pressure p and temperature Tin the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \, K}{T} \cdot V. \tag{17}$$

If the pressure p in the gas reservoir 4 is higher than the pressure $p_{crit}$, which is required to critically operate nozzle 6, the outlet valve 5 can be opened again. By preference, the pressure p in the gas reservoir exceeds $p_{crit}$ by several bars, so that the pressure drop reading can be performed during this phase of overpressure, while nozzle 6 is always operated critically. Outlet valve 5 now closes again, which concludes the pressure drop measurement. By preference, pressure sensor 8 is installed as a differential pressure sensor relative to the outlet 10 of the measuring apparatus. However, it is also possible to provide an additional pressure sensor 8' at the outlet.

During the pressure drop reading, the time-dependent pressure p(t) and the time-dependent temperature T(t) in the pressure reservoir 4 has been measured and recorded by the analyzer unit 11. With these data, the time constant τ in equation (6) or the gas property factor $\Gamma^*$ in equation (7) is determined in the analyzer unit. At the same time, flow data have been measured with the microthermal sensor 7, which were recorded in turn by the analyzer unit to determine the factor S in equation (9) or the gas property factor $\Gamma$ in equation (11). Since the inlet valve and the outlet valve close after the pressure drop reading, no gas flows past the microthermal sensor 7 anymore. Now the measurement of the thermal conductivity reading $\lambda$ can take place. The thermal conductivity $\lambda$, recorded in turn by the analyzer unit, is determined with the aid of equation (12).

Now the (optional) validation of the gas property factor $\Gamma$ or $\Gamma^*$ respectively takes place in the analyzer unit 11. Thereafter, depending on the desired quantity relevant to combustion Q, the calculation of this value by aid of equation (15) with the previously determined correlation function $Q_{corr}=f_{corr}(\Gamma, \Gamma^*, \lambda)$ is made.

Figure 1B:
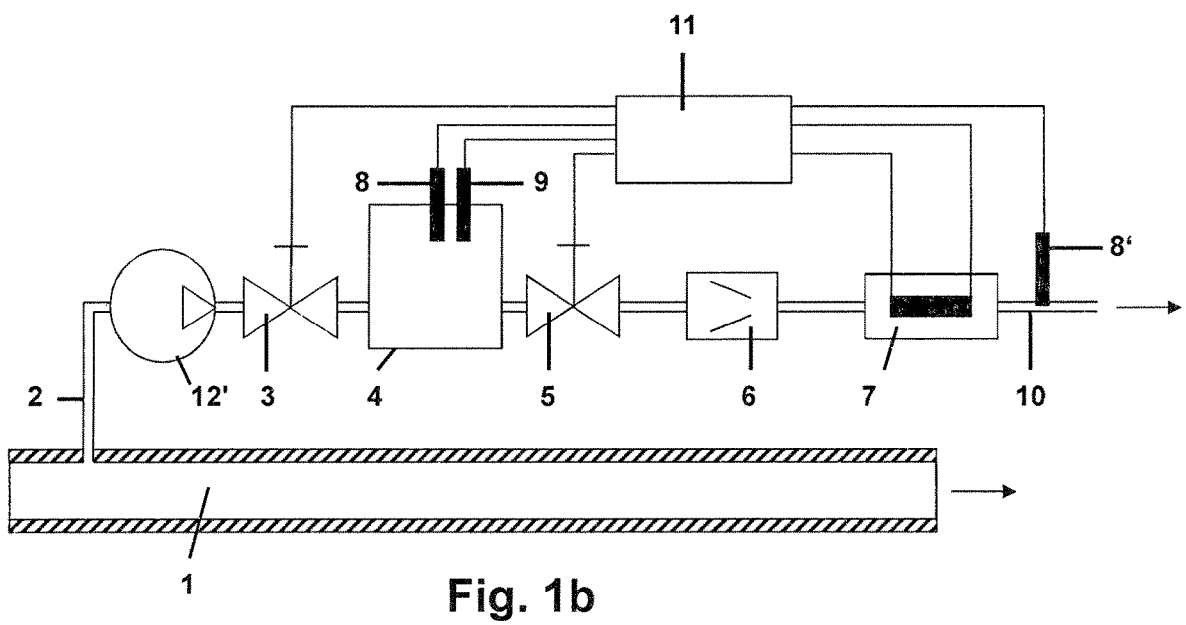
FIG. 1b shows a variant of the exemplary embodiment shown in FIG. 1a, FIG. 2 shows a second exemplary embodiment of the schematic configuration of a measuring apparatus according to the present invention (low pressure variant)

If required, it is possible to provide additionally, as shown in FIG. 1$b$, a compressor 12', installed, for example, on the inlet side of the gas reservoir 4 to increase the pressure in the gas reservoir.

Figure 2:
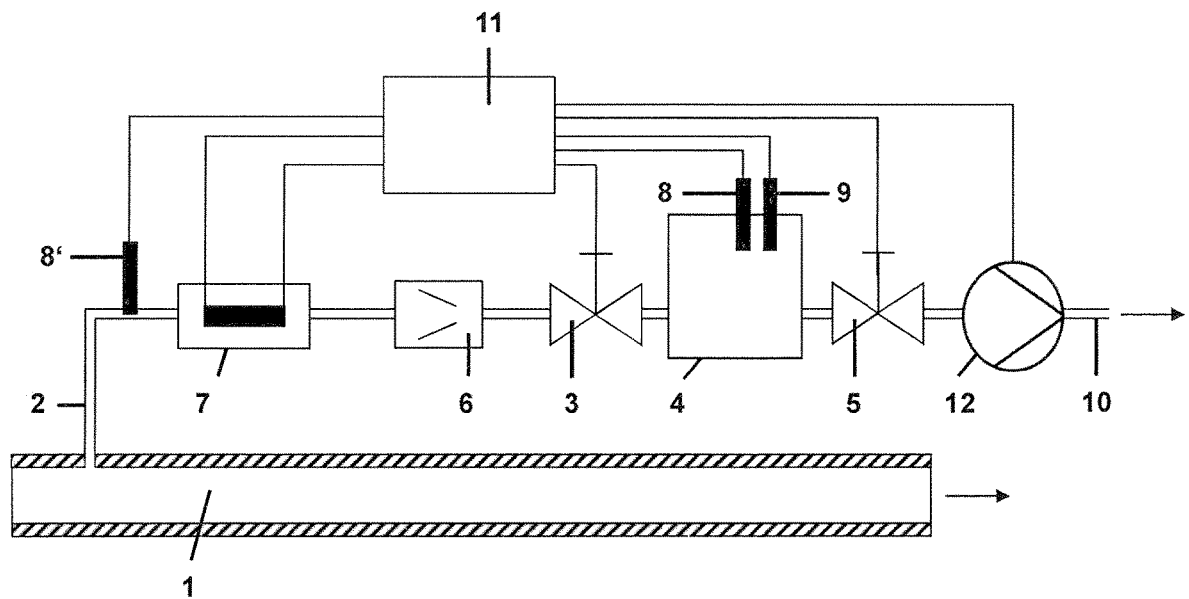

FIG. 2 shows a second exemplary embodiment of the schematic configuration of a measuring apparatus according to the present invention, which is based on low pressure in the gas reservoir. This so-called low pressure variant is advantageous, for example, for the gas supply to end customers. In the second exemplary embodiment, the measuring apparatus comprises, in addition to the gas reservoir 4, a pressure sensor 8 on the gas reservoir, an analyzer unit 11, which is configured to perform a method according to the present invention, a critical nozzle 6 and a microthermal sensor 7 to measure the flow and the thermal conductivity, in which case the gas reservoir 4 is connected with the critical nozzle 6 and the microthermal sensor 7 for the measurement.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

An exemplary embodiment of the method for determining physical properties and/or quantities relevant to combustion of gas or gas mixtures according to the present invention is described below with reference to FIG. 2. In this method, the gas or gas mixture flows under pressure through the critical nozzle 6 and past the microthermal sensor 7 into the gas reservoir 4, with the same mass flow being applied to the critical nozzle and the microthermal sensor. The pressure increase in the gas reservoir 4 is measured as a function of time, and a first gas property factor $\Gamma^*$, dependent on a first group of physical properties of the gas or gas mixture, is determined by reference to the measured values of the pressure increase, with the first gas property factor being derived, for example, from a proportionality constant of the same. A second gas property factor $\Gamma$, dependent on a second group of physical properties of the gas or gas mixture, is calculated from the flow signal of the microthermal sensor 7, with the second gas property factor including, for example, the heat capacity $c_p$ of the gas or gas mixture, or being dependent on the same; Next, the thermal conductivity $\lambda$ of the gas or gas mixture is determined with the aid of the microthermal sensor 7, and the desired physical property or quantity relevant to combustion is determined by aid of correlation on the basis of the first and/or second gas property factor $\Gamma^*$, $\Gamma$ and the thermal conductivity.

Other advantageous embodiments and variants of the method are described in the preceding sections of the specification. The following description provides additional details on the method that may be used if desired.

In a first step, the pressure in gas reservoir 4 is advantageously decreased to such an extent, for example with a vacuum pump 12, that the critical nozzle 6 can be critically operated; in other words, until the pressure in the gas reservoir is less than half the pressure upstream of the critical nozzle. No high vacuum is required. As long as the pressure p and the temperature T can be measured in the gas reservoir 4, it is possible to calculate the gas standard volume that has flown into the gas reservoir. However, it is an advantage if the pressure is by some factor less than required for critical conditions, because this means that the measurement can consume more time accordingly, which makes it possible to determine the proportionality constant more accurately.

For further details on the methods, which may be used if necessary, reference is made to the specification of the first exemplary embodiment, subject to replacement of the term "pressure drop" by the term "pressure increase", where appropriate.

Figure 3:
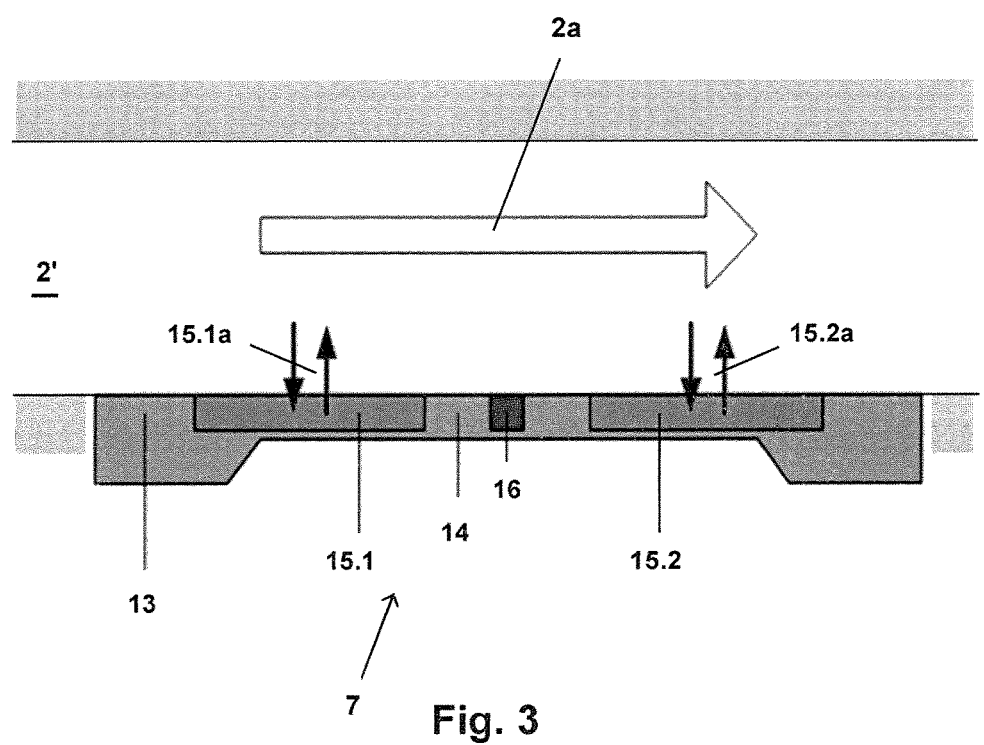
FIG. 3 shows an exemplary embodiment of a microthermal sensor for use in a measuring apparatus according to the present invention.

FIG. 3 shows an exemplary embodiment of a microthermal sensor for use in a measuring apparatus according to the present invention. For example, the microthermal sensor 7 may be—as shown in FIG. 3—an integrated microthermal CMOS hot-wire anemometer that is installed in a section 2' of the test line during normal operation and that can be supplied with a gas or gas mix flow 2*a*. The microthermal CMOS hot-wire anemometer comprises a substrate 13, which typically contains a membrane 14, which measures only a few micrometers in thickness. Furthermore, the CMOS hot wire anemometer consists of two thermal elements 15.1 and 15.2 and a heating element 16, which can be placed between the two thermo-elements in the direction of the flow. The two thermo-elements 15.1., 15.2 serve to record the resulting temperature generated due to the heat exchange 15.1*a*, 15.2*a* in combination with the gas or gas mixture flow 2*a*.

For further details on the functioning of the CMOS hot wire anemometer, reference is made to D. Matter, B. Kramer, T. Kleiner, T. Suter, "Mikroelektronischer Haushaltsgaszähler mit neuer Technologie" (Micro-electronic domestic gas meters using new technologies), in *Technisches Messen* 71, 3 (2004), pp. 137-146.

Figure 4:
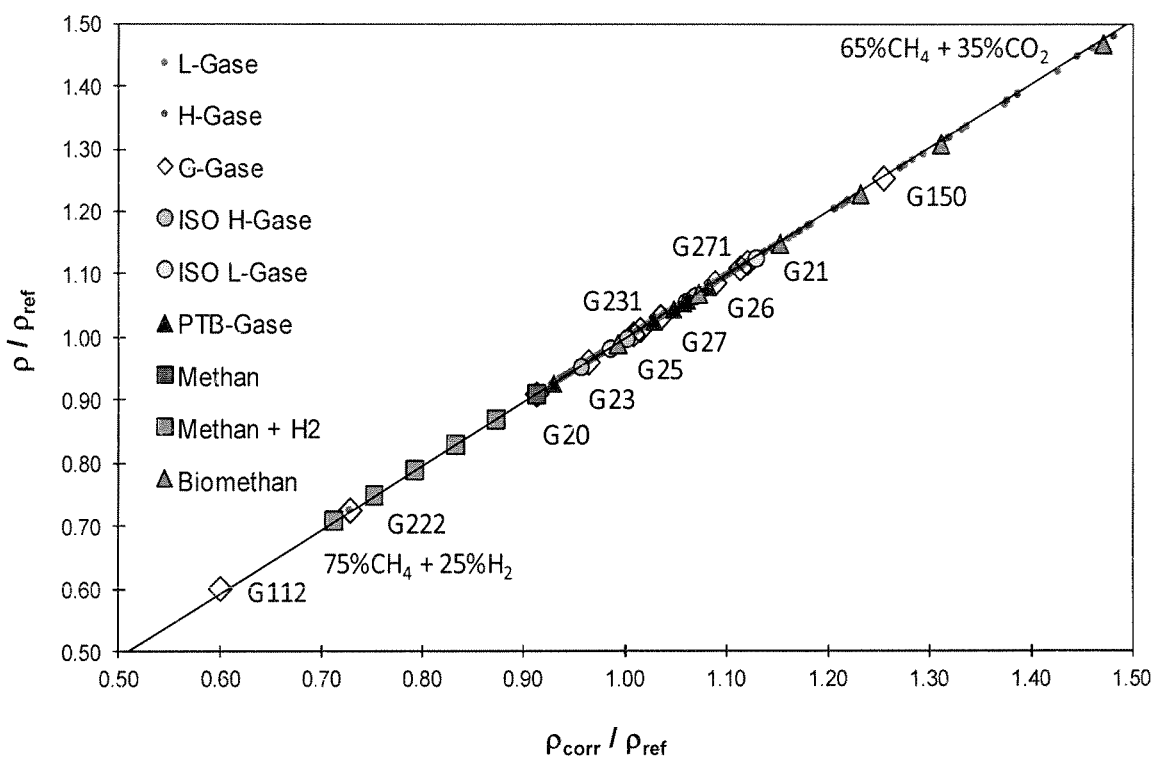
FIG. 4 shows a graphical illustration of the directly measured density ratio (ordinate) as a function of the correlated density ratio (abscissa) for various gas groups at standard conditions (0° C., 1013.25 mbar).

FIG. 4 illustrates the directly measured density ratio $\rho/\rho_{ref}$ (ordinate) as a function of the correlated density ratio $\rho_{corr}/\rho_{ref}$ (abscissa) for various gas groups at standard conditions (0° C., 1013.25 mbar), in which case the correlated density ratio was determined with a method or a measuring apparatus in accordance with the present invention. A typical H-gas was used as a reference gas.

The measuring apparatus described above for determining physical properties and/or quantities relevant to combustion of a gas or gas mixture belongs to a new category, namely "Measurement of the pressure drop or pressure increase in a gas reservoir, wherein the gas flows through a critical nozzle, as well as measurement of thermal conductivity and of flow with the aid of a microthermal sensor, and data validation by summation of the flow values". The components used are inexpensive, which makes it possible to develop new markets, where currently no gas quality sensors are being used for cost reasons. From an accuracy perspective, only a few limitations compared to more expensive, commercially available devices are to be expected, since in this case, too, at least three independent measured variables are being used for the correlation.

Furthermore, the invention comprises in a second embodiment the use of a gas reservoir and a critical nozzle for determining physical properties and/or quantities relevant to combustion of a gas or gas mixture, or a method in which a gas reservoir and a critical nozzle for determining physical properties and/or quantities relevant to combustion of a gas or gas mixture are used, wherein the gas or gas mixture flows under pressure from the gas reservoir through the critical nozzle; in this case, the pressure drop in the reservoir is measured as a function of time, a gas property factor $\Gamma^*$, dependent on the physical properties of the gas or gas mixture, which is derived, for example, from a time constant of the pressure drop, is determined on the basis of the measured variables of the pressure drop, and a desired physical property or quantity relevant to combustion is determined from the gas property factor $\Gamma^*$ through correlation.

The second embodiment of the invention described above can also be seen as a distinct, independent invention.

Figure 5A:
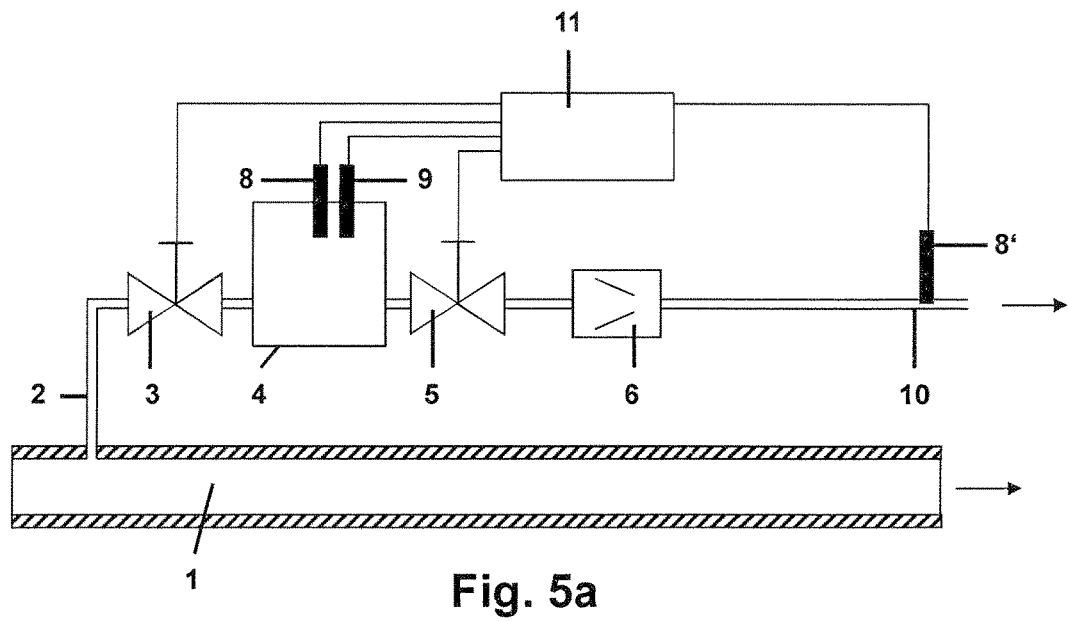
FIG. 5a shows an exemplary embodiment of a schematic configuration of a measuring apparatus according to a second embodiment of the invention (high-pressure variant)

FIG. 5a shows an exemplary embodiment of a schematic configuration of a measuring apparatus according to the second embodiment of the present invention in which the pressure in the main gas duct 1 is higher than the critical pressure for the critical nozzle 6 of the measuring apparatus (high-pressure variation). In the exemplary embodiment the measuring apparatus, in addition to the critical nozzle 6, consists of an analyzer unit 11, which is configured for carrying out a method according to the second embodiment of the invention, and a gas reservoir 4, which is equipped with a pressure sensor 8, in which case the gas reservoir 4 is connected to the critical nozzle 6 for measurement purposes.

If required, the measuring apparatus may comprise one or more of the following additional components: a test line 2, which leads to the gas reservoir 4, and which may be connected to a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be installed on the outlet 10, a temperature sensor 9, which is installed in the gas reservoir, and a compressor 12', which may be located on the inlet side of the gas reservoir 4 to increase the pressure in the gas reservoir.

An exemplary embodiment of the method for determining physical properties and/or quantities relevant to combustion of gas or gas mixtures according to the second embodiment of the invention is described below with reference to FIG. 5a. In this exemplary embodiment, the gas or gas mixture flows from the gas reservoir 4 through the critical nozzle 6. The pressure drop in gas reservoir 4 is measured as a function of time and a first gas property factor $\Gamma^*$, dependent on a first group of physical properties of the gas or gas mixture, is determined on the basis of the measured values of the pressure drop, with the gas property factor being derived, for example, from a time constant of the pressure drop. Furthermore, a desired physical property or quantity relevant to combustion is determined on the basis of the gas property factor $\Gamma^*$ by aid of correlation.

Advantageously, in the second embodiment of the invention, binary gas mixtures are analysed in regard to their content of the two components forming the gas mixture, since the gas property factor $\Gamma^*$ is intrinsically a continuous function of the gas content x % or (1−x %). With the knowledge of content x % or (1−x %), it is then possible to determine physical properties and/or quantities relevant to combustion of the binary gas mixture from sets of tables or by aid of corresponding calculation programs. Of course, it is also possible to directly correlate these physical properties and/or quantities relevant to combustion of the binary gas mixture with the gas property factor $\Gamma^*$.

In an embodiment of the method, it is thus possible to determine the percentage of a component contained in a binary gas mixture, in which case the variable to be correlated corresponds either to the percentage of the component in the composition (x %) and/or any other physical property of the binary gas mixture.

Other advantageous embodiments and variants of the method are described in the preceding sections of the specification. The following description provides additional details on the method that may be used if desired.

Advantageously, the inlet valve 3 and the outlet valve 5 are opened first to allow the gas or gas mixture that is to be measured to flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 5a. In this case, the outlet valve 5 is closed and the gas reservoir 4, the volume content V of which is known, fills up until the inlet valve 3 is covered. Pressure p and temperature T in the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \, K}{T} \cdot V. \tag{17}$$

If the pressure p in the gas reservoir 4 is higher than the pressure $p_{crit}$, which is required to critically operate nozzle 6, the outlet valve 5 can be opened again. By preference, the pressure p in the gas reservoir exceeds $p_{crit}$ by several bars, so that the pressure drop reading can be performed during this phase of overpressure, while nozzle 6 is always operated critically. Outlet valve 5 now closes again, which concludes the pressure drop measurement. By preference, pressure sensor 8 is installed as a differential pressure sensor relative to outlet 10 of the measuring apparatus. However, it is also possible to provide an additional pressure sensor 8' at the outlet.

During the pressure drop reading, the time-dependent pressure p(t) and the time-dependent temperature T(t) in the pressure reservoir 4 has been measured and recorded by the analyzer unit 11. With these data, the time constant τ in equation (6) or the gas property factor $\Gamma^*$ in equation (6') and the gas property factor $\Gamma^*$ in equation (7) or equation (7') is determined in the analyzer unit.

Depending on the desired quantity relevant to combustion Q, this value is now calculated on the basis of equation (15) with the previously determined correlation function $Q_{corr} = f_{corr}(\Gamma^*)$ in analyzer unit 11.

Figure 5B:
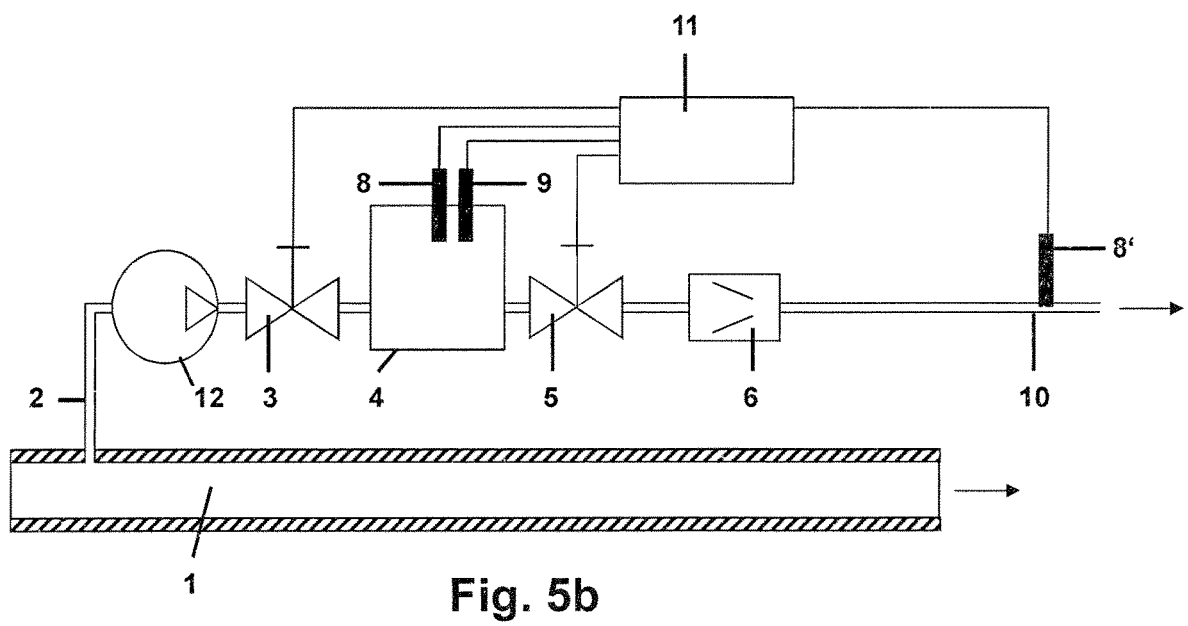
FIG. 5b shows a variant of the exemplary embodiment shown in FIG. 5a, FIG. 6 shows a second exemplary embodiment of a schematic configuration of a measuring apparatus according to a second embodiment of the invention (low pressure variant)

If required, it is possible to provide additionally, as shown in FIG. 5b, a compressor 12', installed, for example, on the inlet side of the gas reservoir 4 to increase the pressure in the gas reservoir.

Figure 6:
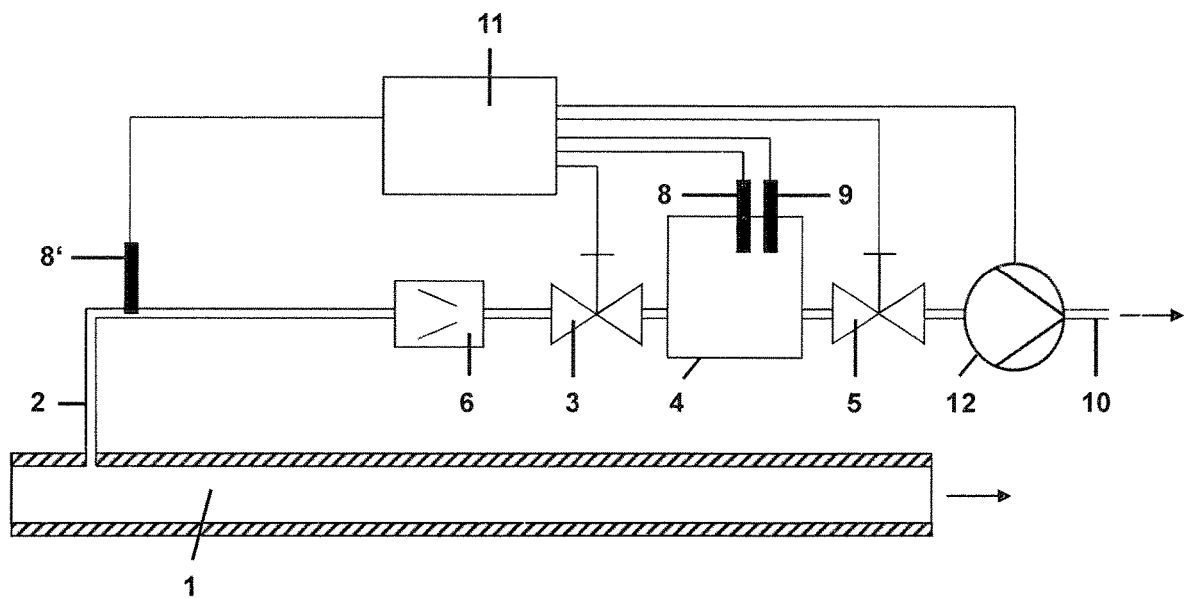

FIG. 6 shows a second exemplary embodiment of the schematic configuration of a measuring apparatus according to the second embodiment of the invention, which is based on low pressure in the gas reservoir. This so-called low pressure variant is advantageous, for example, for the gas supply to end customers. In the second exemplary embodiment, the measuring apparatus, in addition to the gas reservoir 4, comprises a pressure sensor 8, installed on the gas reservoir, an analyzer unit 11, which is configured for carrying out a method according to the second embodiment of the invention, and a critical nozzle 6, in which case the gas reservoir 4 is connected to the critical nozzle 6 for measurement purposes.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

Another exemplary embodiment of the method for determining physical properties and/or quantities relevant to combustion of gas and mixtures according to the second embodiment of the invention is described below with reference to FIG. 6. In this exemplary embodiment, the gas or gas mixture flows under pressure through the critical nozzle 6 into the gas reservoir 4. The pressure increase in the gas reservoir 4 is measured as a function of time, and a gas property factor $\Gamma^*$, dependent on a first group of physical properties of the gas or gas mixture, is determined by reference to the measured values of the pressure increase, with the gas property factor being derived, for example, from a proportionality constant of the pressure increase. A desired physical property or quantity relevant to combustion is determined on the basis of the gas property factor $\Gamma^*$ by aid of correlation.

Other advantageous embodiments and variants of the method are described in the preceding sections of the specification. The following description provides additional details on the method that may be used if desired.

In a preceding step, the pressure in gas reservoir 4 is advantageously decreased to such an extent, for example with a vacuum pump 12, that the critical nozzle 6 can be critically operated; in other words, until the pressure in the gas reservoir is less than half the pressure upstream of the critical nozzle. No high vacuum is required. As long as the pressure p and the temperature T can be measured in the gas reservoir 4, it is possible to calculate the gas standard volume that has flown into the gas reservoir. However, it is an advantage, if the pressure is by some factor less than strictly required for critical conditions, because this means that the measurement proceeds during more time accordingly, which makes it possible to determine the proportionality constant more accurately.

For further details on the methods, which may be used if necessary, reference is made to the specification of the first exemplary embodiment, subject to replacement of the term "pressure drop" by the term "pressure increase", where appropriate.

Figure 7:
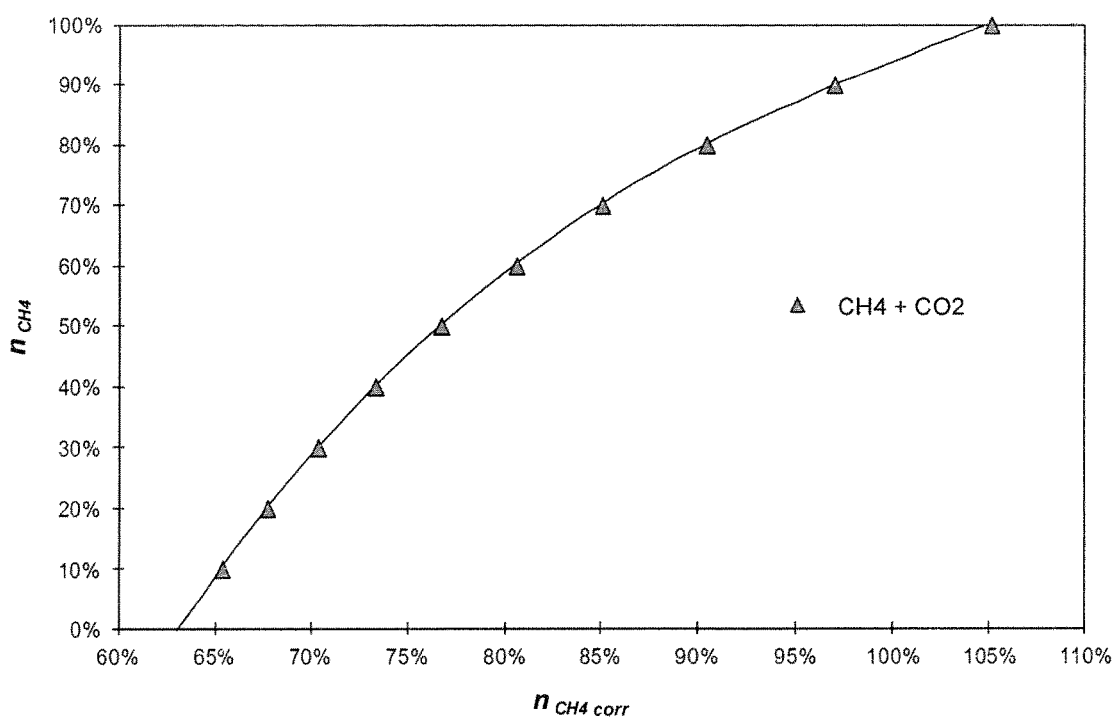
FIG. 7 shows a graphical illustration of the directly measured methane content (ordinate) as a function of the correlated methane content (abscissa) for a binary raw biogas (methane and carbon dioxide).

FIG. 7 illustrates the directly measured methane content $n_{CH4}$ (ordinate) as a function of the correlated methane content $n_{CH4\ corr}$ (abscissa) for a binary raw biogas, composed of methane and carbon dioxide, at standard conditions (0° C., 1013.25 mbar), in which case the correlated methane content was calculated with a method or a measuring apparatus in accordance with the second embodiment of the invention. A typical H-gas was used as a reference gas. The desired variable Q (in this case, the methane content $n_{CH4\ corr}$ in x %) is advantageously determined with the aid of the correlation function $Q_{corr}=a+b\cdot\Gamma^*+c\cdot\Gamma^{*2}+d\cdot\Gamma^{*3}$, in the illustrated example, numerically as a=−7.82, b=22.7, c=−20.4 and d=6.45.

The measuring apparatus described above for determining physical properties and/or quantities relevant to combustion of gas or gas mixtures belongs to a new category, namely "Measurement of the pressure drop or pressure increase in a gas reservoir, wherein the gas flows through a critical nozzle". The components used are inexpensive, which makes it possible to develop new markets, where currently no gas quality sensors are being used for cost reasons. From an accuracy perspective, only a few limitations compared to more expensive, commercially available devices are to be expected, since in this case only one independent measured value, instead of three, is used for the correlation.

In addition, the invention encompasses in a third embodiment the use of a gas reservoir and of a microthermal sensor calibrated for a specific calibration gas or gas mixtures to determine physical properties and/or quantities relevant to combustion of gas or gas mixtures; in this set-up a gas reservoir and a microthermal sensor calibrated for a specific calibration gas or gas mixture for determining physical properties and/or quantities relevant to combustion of gas or gas mixtures are used, with the gas or gas mixture flowing under pressure from the gas reservoir past the microthermal sensor, in which case the volume flow $v_x \cdot A$, determined by the microthermal sensor calibrated for a specific calibration gas or gas mixture, is summed up and compared to the gas volume released from the gas reservoir; from the comparison of the two volumes, a gas property factor $S/v'_x$, dependent on the physical properties of the gas or gas mixture, is determined, in which $v'_x$ represents the flow rate of the released gas volume and in which a desired physical property or quantity relevant to combustion is determined from the gas property factor, which may consist, for example, of $S/v'_x = c_p \cdot \rho/\lambda$ (see equation (9)), through correlation.

The third embodiment of the invention described above can also be seen as a distinct, independent invention.

Figure 8A:
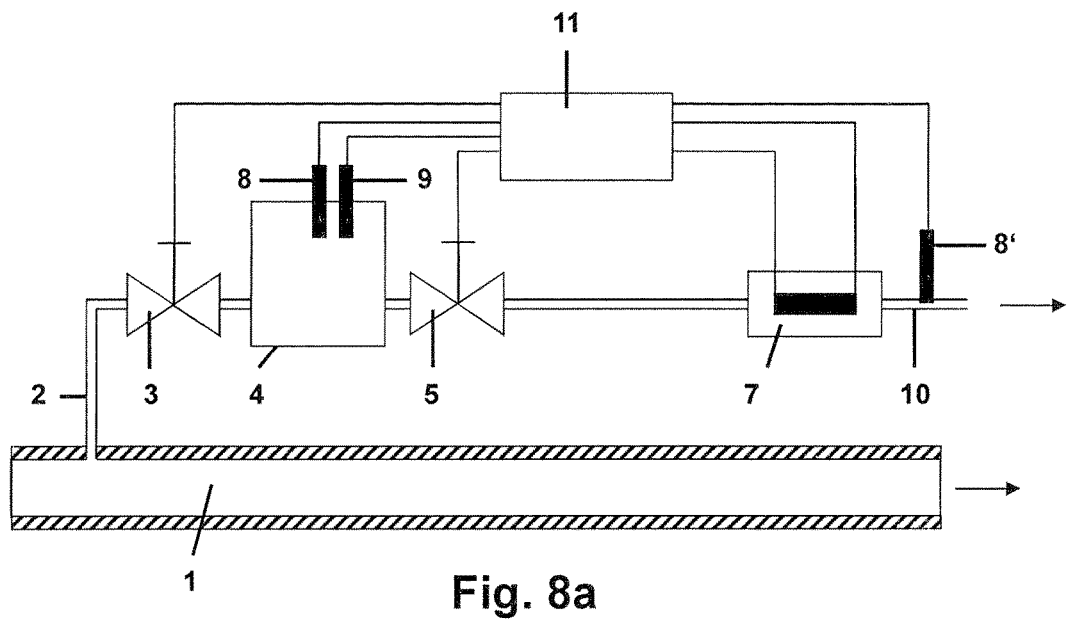
FIG. 8a shows an exemplary embodiment of a schematic configuration of a measuring apparatus according to a third embodiment of the invention with a gas reservoir and a microthermal sensor (high-pressure variant)

FIG. 8a shows an exemplary embodiment of the schematic configuration of a measuring apparatus in accordance with the third embodiment of the invention in case the main gas duct 1 is under pressure (high-pressure variant). In the exemplary embodiment, the measuring apparatus consists of an analyzer unit 11, which is configured for carrying out the method in accordance with the third embodiment of the invention, a gas reservoir 4, which is equipped with a pressure sensor 8 and a microthermal sensor 7 to measure the flow and thermal conductivity, in which case the gas reservoir 4 is connected to the microthermal sensor 7 for measurement purposes.

If required, the measuring apparatus may comprise one or more of the following additional components: a test line 2, which leads to the gas reservoir 4, and which may be connected to a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be installed on the outlet 10, a temperature sensor 9, which is installed in the gas reservoir, and a compressor 12', which may be located on the inlet side of the gas reservoir 4 to increase the pressure in the gas reservoir.

An exemplary embodiment of the method for determining physical properties and/or quantities relevant to combustion of gas or gas mixtures in accordance with the third embodiment of the invention is described below with reference to FIG. 8a. In the method, the gas or gas mixture flows under pressure from the gas reservoir 4 past the microthermal sensor 7, calibrated for a specific calibration gas or gas mixture, in which case the volume flow $v_x \cdot A$ is summed up and compared to the gas volume released from the gas reservoir; from the comparison of the two volumes a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v'_x = c_p \cdot \rho / \lambda$ (see equation (9)), through correlation.

In an advantageous embodiment of the method, the thermal conductivity $\lambda$ of the gas or gas mixture is determined additionally with the aid of the microthermal sensor 7.

Advantageously, with the third embodiment of the invention, natural gas mixtures are examined as to their classification as H-gases or L-gases (gases with a high (H) or low (L) calorific value), since the gas property factor, which may consist, for example, of $S/v'_x = c_p \cdot \rho / \lambda$ (see equation (9)), corresponds to the reciprocal value of the thermal diffusivity of the gas mixture, with the aid of which—together with the thermal conductivity $\lambda$, which can be measured separately with the microthermal sensor—a distinction between H-gas group and L-gas group can be made.

The classification of a natural gas mixture as belonging to the H-gas or L-gas group can be determined, for example, by identifying the gas property factor $(S/v'_x)$ with the reciprocal value of the thermal diffusivity $c_p \cdot \rho / \lambda$, and wherein the classification is made, subject to thermal conductivity, on the basis of a limit value for the thermal diffusivity; above the limit value, a gas mixture is classified as L-gas, and below the limit value, as H-gas.

Thus, in an embodiment variant of the method, the thermal conductivity $\lambda$ of the gas or gas mixture is determined additionally with the aid of the microthermal sensor 7, and a classification of the measured gas as H-gas or L-gas is made in conjunction with the gas property factor $S/v'_x = c_p \cdot \rho / \lambda$.

Other advantageous embodiments and variants of the method are described in the preceding sections of the specification. The following description provides additional details on the method that may be used if desired.

Advantageously, the inlet valve 3 and the outlet valve 5 are opened first to allow the gas or gas mixture that is to be measured flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 8a. In this case, the outlet valve 5 is closed and the gas reservoir 4, the volume content V of which is known, fills up until the inlet valve 3 is closed. Pressure p and temperature T in the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \text{ } K}{T} \cdot V. \tag{17}$$

The outlet valve 5 can now be opened again. By preference, the pressure p in the gas reservoir 4 is higher than the downstream pressure after the gas reservoir by such a rate that the timespan in which the gas from the gas reservoir 4 flows past the microthermal sensor 7 is long enough to ensure that the volume flow $v_x \cdot A$ can be summed up with sufficient accuracy. Outlet valve 5 now closes again, which concludes the flow measurement. By preference, pressure sensor 8 is installed as a differential pressure sensor opposite outlet of the measuring apparatus. However, it is also possible to provide an additional pressure sensor 8' at the outlet.

Flow data have been measured with the microthermal sensor 7 during the flow measurement and recorded by the analyzer unit 11 to determine factor S in equation (9). Since the inlet valve and the outlet valve close after the flow reading, no gas flows past the microthermal sensor 7 anymore. Now the measurement of the thermal conductivity reading $\lambda$ can take place. The thermal conductivity $\lambda$, recorded in turn by the analyzer unit, is determined with the aid of equation (12).

With these data, the volume flow is summed up in the analyzer unit 11 to form volume $V_{sum}$ and to compare it to the gas volume $V_{diff}$ released from the gas reservoir. Based on the comparison of these two volumes, it is now possible to determine a gas property factor $S/v'_x$, dependent on the physical properties of the gas or gas mixture, in which $v'_x$ represents the flow rate derived from the released gas volume. For practical reasons, the volumes for the comparison are converted to standard conditions for the purposes of the comparison by aid of equation (17), with the result that $v'_x$ consists of $$v'_x = v_x \cdot V_{diff}^{norm} / V_{sum}^{norm} \tag{18}$$

with the released gas volume $V_{diff}^{norm}$ converted to standard conditions and the accumulated volume converted to standard conditions $V_{sum}^{norm}$. Thereafter, depending on the desired quantity Q relevant to combustion, this value is now calculated in the analyzer unit 11 with the aid of equation (15) with the previously determined correlation function $Q_{corr} = f_{corr}(S/v'_x)$, or the value of $S/v'_x$ is being used to classify, in conjunction with the thermal conductivity $\lambda$, a natural gas mixture in the category H-gas or L-gas.

Figure 8B:
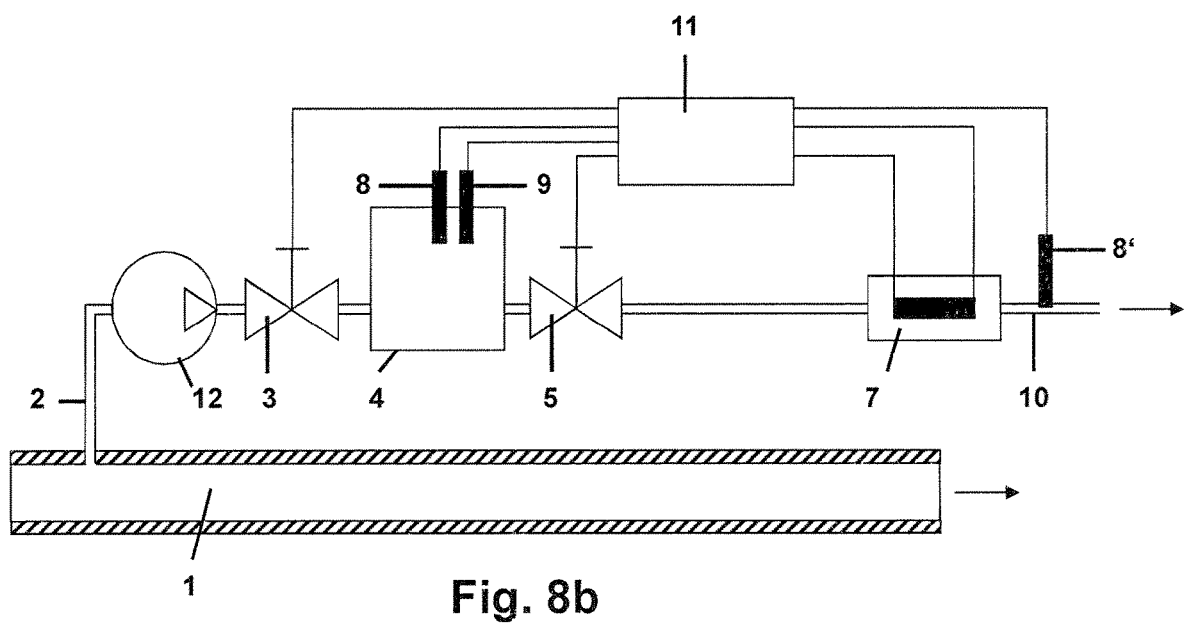
FIG. 8b shows a variant of the exemplary embodiment shown in FIG. 8a, FIG. 9 shows a second exemplary embodiment of a schematic configuration of a measuring apparatus according to a third embodiment of the invention with a gas reservoir and a microthermal sensor (low pressure variant)

If required, it is possible to provide additionally, as shown in FIG. 8b, a compressor 12', installed, for example, on the inlet side of the gas reservoir 4 to increase the pressure in the gas reservoir.

Figure 9:
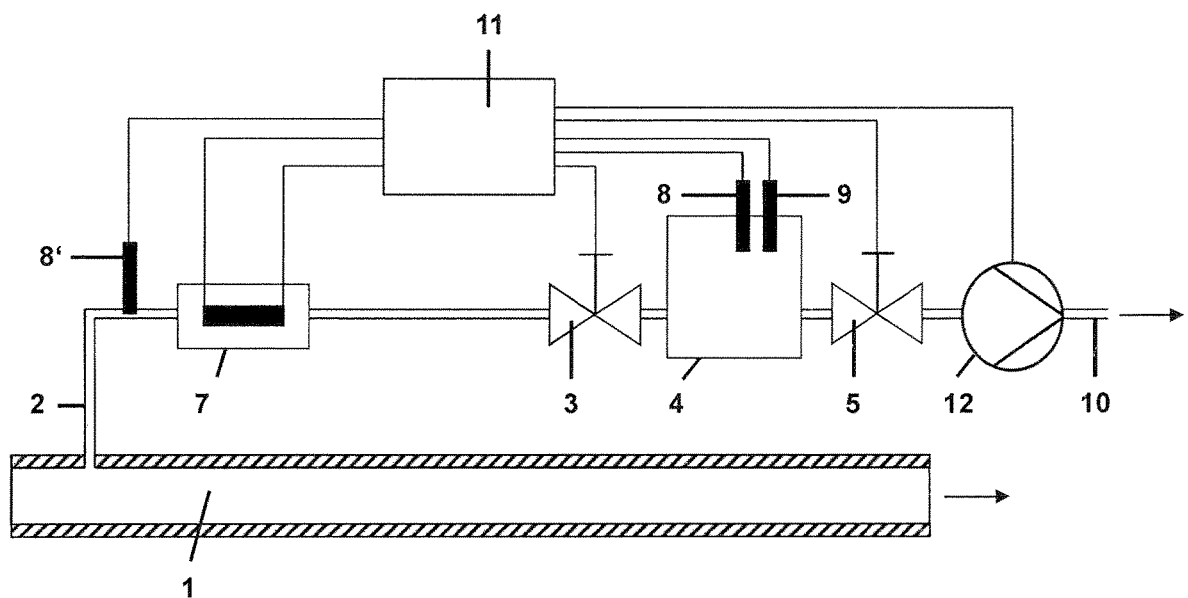

FIG. 9 shows a second exemplary embodiment of the schematic configuration of a measuring apparatus according to the third embodiment of the invention, which is based on low pressure in the gas reservoir. This so-called low pressure variant is advantageous, for example, for the gas supply to end customers. In the second exemplary embodiment, the measuring apparatus comprises, in addition to the gas reservoir 4, a pressure sensor 8 on the gas reservoir, an analyzer unit 11, which is configured to carry out a method according to the third embodiment of the invention and a microthermal sensor 7 to measure the flow and the thermal conductivity, in which case the gas reservoir 4 is connected to the microthermal sensor 7 for the purposes of the measurement.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

Another exemplary embodiment of the method for determining physical properties and/or quantities relevant to combustion of gas and mixtures in accordance with the third embodiment of the invention is described below with reference to FIG. 9. In this exemplary embodiment, the gas or gas mixtures flows at a pressure that is typically higher than the downstream pressure after the gas reservoir by such a rate that the timespan in which the gas from the gas reservoir 4 flows past the microthermal sensor 7 is long enough to ensure that the volume flow $v_x \cdot A$ can be summed up with sufficient accuracy. The summed-up volume flow $V_{sum}$, is compared to the gas volume $V_{diff}$ released from the gas reservoir, and from the comparison of the two volumes, a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v' = c_p \cdot \rho/\lambda$ (see equation (9)), through correlation.

A further exemplary embodiment of the method for determining physical properties and/or quantities relevant to combustion of gas and mixtures in accordance with the third embodiment of the invention is described below with reference to FIG. 9. In this exemplary embodiment, the gas or gas mixtures flows under pressure past the microthermal sensor 7 into the gas reservoir 4. The volume flow $v_x \cdot A$ of the gas or gas mixture, determined on the basis of the flow rate ($v_x$) measured with the microthermal sensor, is summed up and the summed up volume flow compared to the gas volume $V_{diff}$ fed into the gas reservoir. From the comparison of the two volumes, a gas property factor $S/v'_x$, dependent on the physical properties of the gas or gas mixture, is derived, in which $v'_x$ represents the flow rate determined from the fed gas volume, and a desired physical property or quantity relevant to combustion is determined from the gas property factor through correlation.

Thus, in an advantageous embodiment of the method, the thermal conductivity $\lambda$ of the gas or gas mixture is determined with the aid the microthermal sensor 7, and a classification of the measured gas as H-gas or L-gas is made, for example, in conjunction with the gas property factor $S/v'_x = c_p \cdot \rho/\lambda$.

For other advantageous embodiments and variants of the method, and for further details on the methods, which may be used if required, reference is made to the preceding sections of the specification, subject to replacement of the term "pressure drop" by the term "pressure increase", where appropriate.

Figure 10:
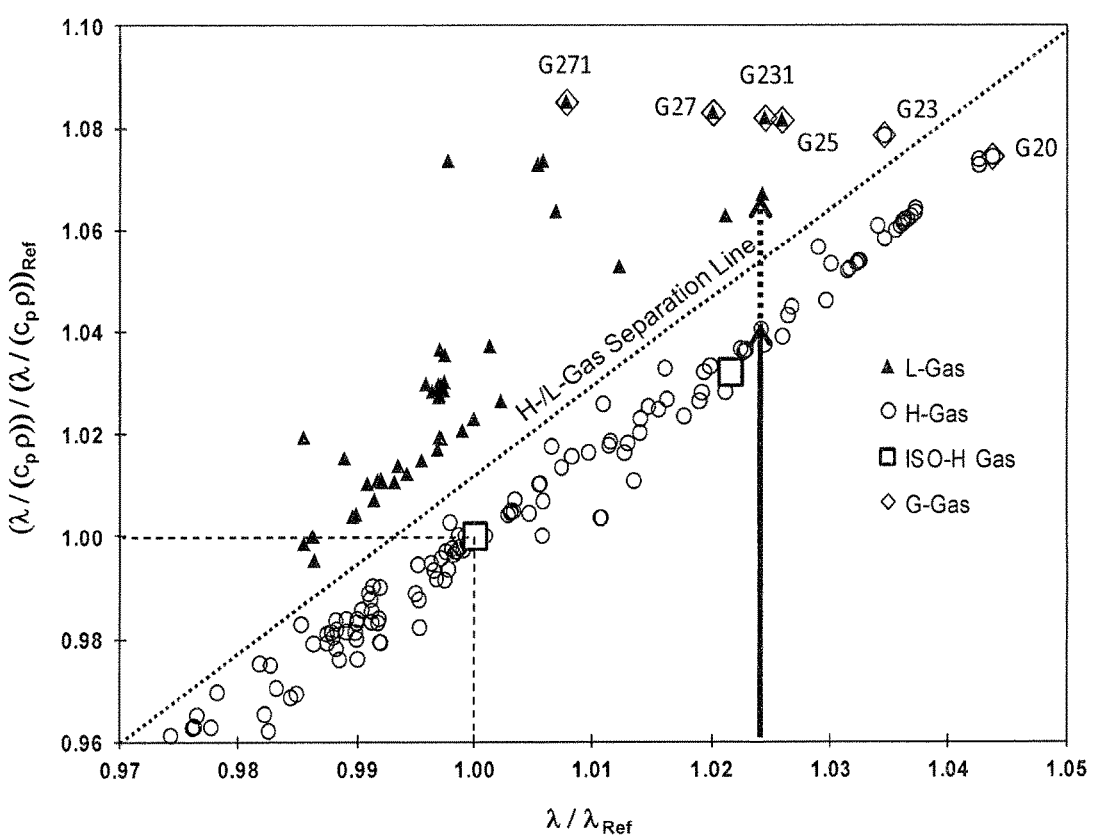
FIG. 10 shows a graphical illustration of the classification of natural gas mixtures by reference to thermal diffusivity (ordinate) with simultaneous knowledge of the thermal conductivity A (abscissa).
Figure 11:
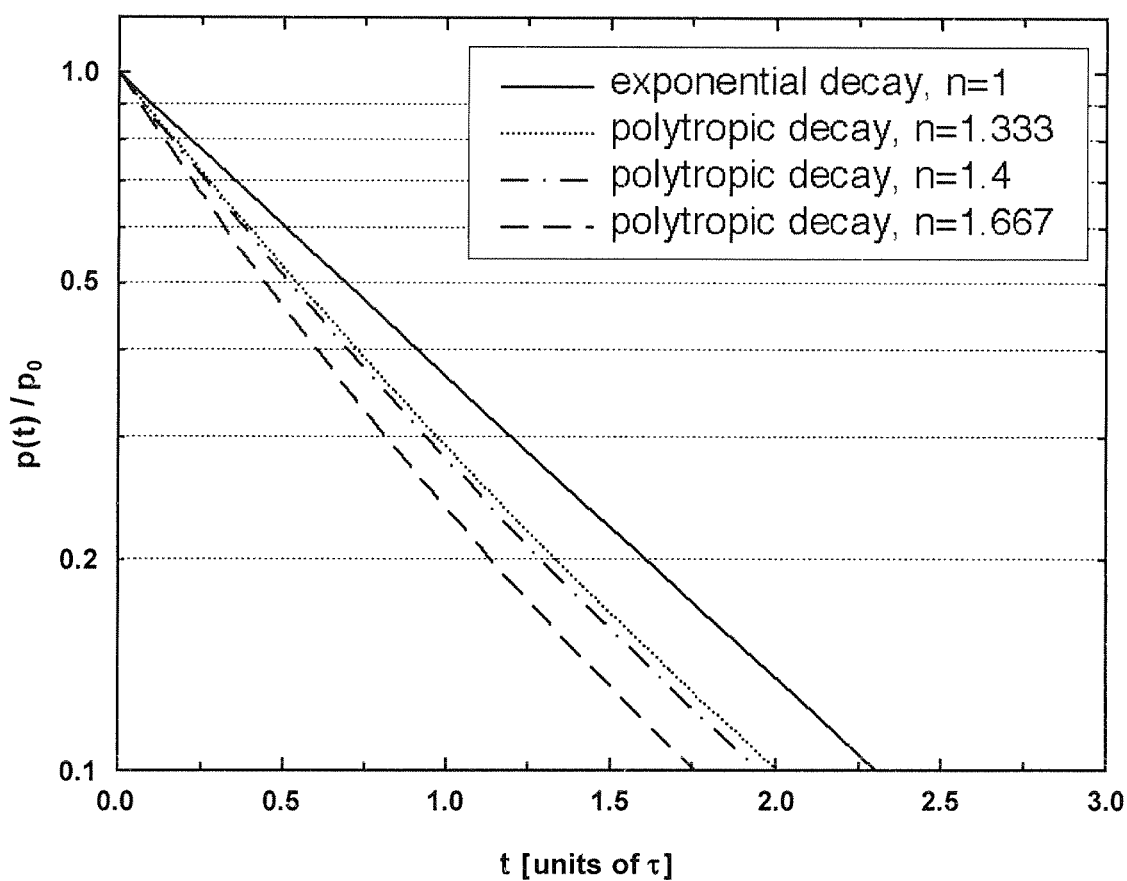
FIG. 11 shows pressure decay curves calculated for different polytropic indices with the pressure being displayed on a logarithmic ordinate.

FIG. 10 illustrates how a classification as H-gas or L-gas can be made by means of known thermal conductivities $\lambda$ (abscissa) and thermal diffusivities $\lambda/(c_p\rho)$, also referred to as temperature conductivities (ordinate). L-gases above the H/L-gas separation line typically have higher thermal diffusivities than H-gases with the same thermal conductivity below the separation line (double arrow at x≈1.024). Since the gas property factor $S/v'_x = c_p \cdot \rho/\lambda$ is essentially equivalent to the reciprocal value of the thermal diffusivity of the gas mixture, it is thus possible to make the distinction between H-gas and L-gas with the aid of the additionally measured thermal conductivity $\lambda$. All values are shown at standard conditions (0° C., 1013.25 mbar). A typical H-gas was used as reference gas (dashed line for the coordinate (1.00,1.00)).

The measuring apparatus described above for determining physical properties and/or quantities relevant to combustion of gas or gas mixtures belongs to a new category, namely "Thermal conductivity and flow measurement with the aid of a microthermal sensor, cumulative adding of the flow values and a comparison of the released volume from a reference volume. Thereafter, classification of natural gases as H-gas or L-gas". The components used are inexpensive, which makes it possible to develop new markets, where currently no gas quality sensors are being used for cost reasons. From an accuracy perspective, only a few limitations compared to more expensive, commercially available devices are to be expected, since this apparatus uses only two instead of three independent measured variables for the correlation.

The invention claimed is:

1. A method for determining physical properties and/or quantities relevant to combustion of gas and/or gas mixtures, the method comprising:

flowing a gas or gas mixture from a gas reservoir or into a gas reservoir with the gas or gas mixture flowing under pressure through a critical nozzle and past a microthermal sensor, wherein the same mass flow is applied to the critical nozzle and the microthermal sensor;

measuring pressure drop or pressure increase respectively in the gas reservoir as a function of time;

determining a first gas property factor ($\Gamma^*$), which is dependent on a first group of physical properties of the gas and/or gas mixture, on the basis of measured values of the pressure drop or pressure increase;

determining a second gas property factor ($\Gamma$), which is dependent on a second group of physical properties of the gas or gas mixture, from a flow signal generated by the microthermal sensor;

determining the thermal conductivity ($\lambda$) of the gas and/or gas mixture using the microthermal sensor; and determining a physical property and/or quantity relevant to combustion from the first and second gas property factor ($\Gamma^*$, $\Gamma$) and the thermal conductivity ($\lambda$) through correlation.

2. The method according to claim 1, in which the first gas property factor ($\Gamma^*$) is derived from the time constant of the pressure drop on the basis of an exponential decline of the measured pressure, or in which the first gas property factor ($\Gamma^*$) is derived from a proportionality constant of the pressure increase on the basis of a linear increase of the measured pressure.

3. The method according to claim 1, in which the first gas property factor ($\Gamma^*$) is derived from a time constant of the pressure drop or pressure increase respectively on the basis of an adiabatic decline or increase of the measured pressure.

4. The method according to claim 1, in which the second gas property factor ($\Gamma$) contains the quotient of heat capacity ($c_p$) divided by thermal conductivity ($\lambda$) of the gas or gas mixture, or is dependent on the same.

5. The method according to claim 1, in which the first and/or the second gas property factor are derived by additionally measuring the nozzle inlet pressure ($p_{Nozzle}$) and/or the temperature (T) or initial temperature ($T_0$) and by omitting all gas-unrelated variables.

6. The method according to claim 1, wherein the gas property factors ($\Gamma^*$, $\Gamma$) are validated by comparing the values for the total volume of the gas or gas mixture released from or fed into the gas reservoir by:
   measuring the pressure and temperature in the gas reservoir at the start and end of the pressure drop or pressure increase reading and by determining the standard volume released or fed respectively by reference to the known volume of the gas reservoir;
   summing up the standard flow measured with the microthermal sensor during the time interval between the start and end of the pressure drop or pressure increase reading;
   comparing the standard volume released or fed respectively to the summed up standard volume; and
   in case of a discrepancy, adjusting the first and/or the second gas property factor ($\Gamma^*$, $\Gamma$) and/or adjusting the pressure signal and/or the standard flow variable of the microthermal sensor.

7. The method according to claim 1, in which the flow signal of the microthermal sensor is calibrated by at least:
   calibrating the flow signal of the microthermal sensor for a specific calibration gas or gas mixture;
   determining the ratio ($\Gamma/\Gamma^*$) of the second gas property factor, determined on the basis of the flow signal of the microthermal sensor, to the first gas property factor for an unknown gas or gas mixture; and
   comparing the standard volume values from the reading of the pressure drop or pressure increase and the reading of the summed up standard flow of the microthermal sensor, which are then used to adjust the ratio of the second gas property factor to the first, and to adapt the value for the second gas property factor ($\Gamma$).

8. The method according to claim 1 where the desired physical property is the density or the thermal conductivity or the heat capacity or the viscosity of the gas or gas mixture, and/or where the quantity relevant to combustion is the energy content or the calorific value or the Wobbe index or the methane number or the air requirement of the gas or gas mixture.

9. The method according to claim 1, wherein a polytropic index (n) is determined on the basis of measured values of the pressure drop or pressure increase respectively, and the physical property and/or quantity relevant to combustion is further determined from the polytropic index (n).

10. The method according to claim 1, where the desired physical property or the quantity relevant to combustion (Q) is determined by aid of a correlation function $$Q = f_{corr}(\Gamma, \Gamma^*, \lambda) = const \cdot \Gamma^r \cdot \Gamma^{*s} \cdot \lambda^t \text{ or}$$

$$Q = f_{corr}(\Gamma, \Gamma^*, \lambda, n) = const \cdot \Gamma^r \cdot \Gamma^{*s} \cdot \lambda^t \cdot n^u,$$

wherein r, s, t and u are exponents, and const is a constant.

11. A measuring apparatus configured to perform the method of claim 1, the measuring apparatus comprising:
   an analyzer unit configured to determine the first gas property factor, the second gas property factor, the thermal conductivity, and the physical property and/or quantity relevant to combustion,
   the gas reservoir that is equipped with a pressure sensor, the critical nozzle that is configured to be coupled, via a gas duct, to the gas reservoir allowing the gas or gas mixture to flow under pressure, and
   the microthermal sensor.

12. The measuring apparatus according to claim 11, comprising a compressor to increase the pressure in the gas reservoir or a vacuum pump to generate low pressure in the gas reservoir.

13. The measuring apparatus according to claim 11, wherein the gas reservoir is equipped with a heat exchanger to approximate isothermal conditions or with a heat insulation to limit heat exchange in the adiabatic or near adiabatic case.

14. A method to use a gas reservoir and a critical nozzle for determining physical properties and/or quantities relevant to combustion of gas or gas mixtures, the method comprises:
   flowing a gas or gas mixture from the gas reservoir or into the gas reservoir with the gas or gas mixture flowing under pressure through the critical nozzle, and, in the case the gas or gas mixture is flowing from the gas reservoir, with a decreasing mass flow of the gas or gas mixture when pressure is decreasing in the gas reservoir;
   measuring the pressure drop or pressure increase respectively in the gas reservoir as a function of time, wherein a nozzle inlet pressure of the critical nozzle is higher than a critical pressure of the critical nozzle during the measuring of the pressure drop or pressure increase respectively in the gas reservoir;
   determining a gas property factor ($\Gamma^*$), which is dependent on the physical properties of the gas or gas mixture, on the basis of measured values of the pressure drop or pressure increase; and
   determining a desired physical property or quantity relevant to combustion on the basis of the gas property factor ($\Gamma^*$) through correlation.

15. The method according to claim 14, in which the gas property factor ($\Gamma^*$) is derived from the time constant of the pressure drop on the basis of an exponential decline of the measured pressure, or in which the gas property factor ($\Gamma^*$) is derived from a proportionality constant of the pressure increase on the basis of a linear increase of the measured pressure.

16. The method according to claim 14, in which the first gas property factor ($\Gamma^*$) is derived from a time constant of the pressure drop or pressure increase respectively on the basis of an adiabatic decline or increase of the measured pressure.

17. The method according to claim 14, in which the gas property factor is determined by additionally measuring the nozzle inlet pressure ($p_{Nozzle}$) and/or the temperature (T) or initial temperature ($T_0$) and by omitting all gas-unrelated variables.

18. The method according to claim 14 wherein a polytropic index (n) is determined on the basis of measured values of the pressure drop or pressure increase respectively, and/or wherein the physical property and/or quantity relevant to combustion through correlation is further determined on the basis of the polytropic index (n).

19. The method according to claim 14, wherein the desired physical property or quantity relevant to combustion is determined only on the basis of the gas property factor ($\Gamma^*$).

20. A measuring apparatus configured to perform the method of claim 14, the measuring apparatus comprising:

an analyzer unit configured to determine the gas property factor and to determine the desired physical property or quantity relevant to combustion, the gas reservoir that is equipped with a pressure sensor, and the critical nozzle that is configured to be coupled, via a gas duct, to the gas reservoir allowing the gas or gas mixture to flow under pressure.

21. The measuring apparatus according to claim 20, comprising a compressor to increase the pressure in the gas reservoir or a vacuum pump to generate low pressure in the gas reservoir.

22. The measuring apparatus according to claim 20, wherein the gas reservoir is equipped with a heat exchanger to approximate isothermal conditions or with a heat insulation to limit heat exchange in the adiabatic or near adiabatic case.

23. A method to use a gas reservoir and a critical nozzle for determining physical properties and/or quantities relevant to combustion of gas or gas mixtures, the method comprises:

flowing a gas or gas mixture from the gas reservoir or into the gas reservoir with the gas or gas mixture flowing under pressure through the critical nozzle, and, in the case the gas or gas mixture is flowing from the gas reservoir, with a decreasing mass flow of the gas or gas mixture when pressure is decreasing in the gas reservoir;

measuring the pressure drop or pressure increase respectively in the gas reservoir as a function of time;

determining a gas property factor ($\Gamma^*$), which is dependent on the physical properties of the gas or gas mixture, on the basis of measured values of the pressure drop or pressure increase; and determining a desired physical property or quantity relevant to combustion on the basis of the gas property factor ($\Gamma^*$) through correlation, wherein a polytropic index (n) is determined on the basis of measured values of the pressure drop or pressure increase respectively, and/or wherein the physical property and/or quantity relevant to combustion through correlation is further determined on the basis of the polytropic index (n).

24. A measuring apparatus configured to perform the method of claim 23, the measuring apparatus comprising:

an analyzer unit configured to determine the gas property factor and the polytropic index and to determine the desired physical property or quantity relevant to combustion, the gas reservoir that is equipped with a pressure sensor, and the critical nozzle that is configured to be coupled, via a gas duct, to the gas reservoir allowing the gas or gas mixture to flow under pressure.

\* \* \* \* \*

UNITED STATES PATENT AND TRADEMARK OFFICE
CERTIFICATE OF CORRECTION

PATENT NO. : 10,816,525 B2
APPLICATION NO. : 15/610000
DATED : October 27, 2020
INVENTOR(S) : Philippe Pretre et al.

Page 1 of 2

It is certified that error appears in the above-identified patent and that said Letters Patent is hereby corrected as shown below:

In the Specification

Column 4, Line 8, change "(3)" to --($\underline{3}$)--;

Column 4, Line 30, change "(4)" to --($\underline{4}$)--;

Column 4, Line 40, change "
$$\frac{\dot{p} \cdot p^{(n-1)/n} - p \cdot (n-1)/n \cdot p^{-1/n} \cdot \dot{p}}{p^{2(n-1)/n}} = -c \cdot C_d \cdot A^* \cdot \psi_{max} \cdot \sqrt{\frac{M}{T \cdot R_m}} \cdot p \cdot \frac{R_m}{M \cdot V}$$
$$= -C_d \cdot \frac{A^*}{V} \cdot \psi_{max} \cdot \sqrt{\frac{c \cdot R_m}{M}} \cdot p^{(1-n)/2n} \cdot p \qquad (\underline{5})$$
" to
--
$$\frac{\dot{p} \cdot p^{(n-1)/n} - p \cdot (n-1)/n \cdot p^{-1/n} \cdot \dot{p}}{p^{2(n-1)/n}} = -c \cdot C_d \cdot A^* \cdot \psi_{max} \cdot \sqrt{\frac{M}{T \cdot R_m}} \cdot p \cdot \frac{R_m}{M \cdot V}$$
$$= -C_d \cdot \frac{A^*}{V} \cdot \psi_{max} \cdot \sqrt{\frac{c \cdot R_m}{M}} \cdot p^{(1-n)/2n} \cdot p \qquad (\underline{5})$$
--;

Column 4, Line 50, change "(5)" to --($\underline{5}$)--;

Column 4, Line 61, change "(5.1)" to --($\underline{5.1}$)--;

Column 5, Line 37, change "equation (5) converges into equation (5)" to --equation ($\underline{5}$) converges into equation (5)--;

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)

Column 5, Line 41, change "(5.4)" to --(5.4)--;

Column 6, Line 44, change "(5')" to --(5')--;

Column 6, Line 49, change

"$$\frac{\dot{p} \cdot p^{(n-1)/n} - p \cdot (n-1)/n \cdot p^{-1/n} \cdot \dot{p}}{p^{2(n-1)/n}} = +c \cdot C_d \cdot A^* \cdot \psi_{max} \cdot \sqrt{\frac{M}{T \cdot R_m}} \cdot p_{nozzle} \cdot \frac{R_m}{M \cdot V}$$

$$= C_d \cdot \frac{A^*}{V} \cdot \psi_{max} \cdot \sqrt{\frac{c \cdot R_m}{M}} \cdot p_{nozzle} \cdot p^{(1-n)/2n} \quad (5')$$"

to

--$$\frac{\dot{p} \cdot p^{(n-1)/n} - p \cdot (n-1)/n \cdot p^{-1/n} \cdot \dot{p}}{p^{2(n-1)/n}} = +c \cdot C_d \cdot A^* \cdot \psi_{max} \cdot \sqrt{\frac{M}{T \cdot R_m}} \cdot p_{nozzle} \cdot \frac{R_m}{M \cdot V}$$

$$= C_d \cdot \frac{A^*}{V} \cdot \psi_{max} \cdot \sqrt{\frac{c \cdot R_m}{M}} \cdot p_{nozzle} \cdot p^{(1-n)/2n} \quad (5')$$--;

Column 7, Line 28, change "(5.4')" to --(5.4')--;

Column 7, Line 37, change "(6')" to --(6')--;

Column 9, Line 26, change "constant r" to --constant τ--;

Column 9, Line 57, change "(15)" to --(15)--;

Column 9, Line 60, change "(16)" to --(16)--;

Column 18, Line 37, change "temperature Tin" to --temperature T in--;

Column 22, Line 32, change "temperature Tin" to --temperature T in--;

Column 25, Line 67, change "temperature Tin" to --temperature T in--; and

Column 28, Line 1, change "Δ/($c_p$p)" to --$\lambda/(c_p\rho)$--.